United States Patent [19]

Herman

[11] 4,412,288

[45] Oct. 25, 1983

[54] EXPERIMENT-MACHINE

[76] Inventor: Michael Herman, 3059 Brighton 5th St., Brooklyn, N.Y. 11235

[21] Appl. No.: 136,326

[22] Filed: Apr. 1, 1980

[51] Int. Cl.$^3$ .............................................. A61B 5/00
[52] U.S. Cl. .................................. 364/413; 128/634; 378/4
[58] Field of Search ............... 364/413, 414, 415, 200, 364/900; 128/630, 653, 634; 250/445 R, 445 T

[56] References Cited

U.S. PATENT DOCUMENTS

| | | | |
|---|---|---|---|
| 3,697,956 | 10/1972 | Goldman et al. ................... | 364/200 |
| 3,916,176 | 10/1975 | Alien et al. ......................... | 364/415 |
| 3,977,394 | 8/1976 | Jones et al. ......................... | 364/415 |
| 4,048,501 | 9/1977 | Grenier ............................... | 364/414 |
| 4,094,307 | 6/1978 | Young, Jr. .......................... | 364/415 |
| 4,111,557 | 4/1978 | Rottenkolber et al. ............. | 356/168 |
| 4,112,491 | 9/1978 | Bugay ................................. | 364/415 |
| 4,122,518 | 10/1978 | Castleman et al. ................. | 364/415 |
| 4,135,247 | 1/1979 | Gordon et al. ................. | 250/445 T |
| 4,155,258 | 5/1979 | Engeler et al. ..................... | 364/415 |
| 4,181,939 | 1/1980 | Lyons ................................. | 364/200 |
| 4,186,748 | 2/1980 | Schlager ............................. | 364/415 |
| 4,213,462 | 7/1980 | Sato .................................... | 128/634 |
| 4,245,646 | 1/1981 | Ionnou et al. ...................... | 128/653 |

OTHER PUBLICATIONS

Yoshiya et al., Spectrophotometric Monitoring of Arterial Oxygen Saturation in the Fingertip, Medical & Biological Engineering and Computing, Jan. 1980, vol. 18, No. 1, pp. 27-32.
Goldman, Laser Medical Instrumentation, Medical Instrumentation, vol. 10, No. 2, Mar.-Apr. 1976, pp. 125-129.
Cobbold, Transducers for Biomedical Measurements, John Wiley & Sons, 1974, 322-232.
Stibitz et al., Indirect Measurement of Intracellular Conductivity, IEEE Transactions on Biomedical Engineering, vol. BME-24, No. 3, pp. 300-302.
Gilbert et al., A Real-Time Hardware System for Digital Processing of Wide-Band Video Images, IEEE Trans. on Computer, vol. C-25, No. 11, Nov. 1976, pp. 1089-1100.
Bacharach et al., A Real-Time System for Multi-Image Gated Cardiac Studies, Journal of Nuclear Medicine, vol. 18, No. 1, 1977, pp. 79-84.

Primary Examiner—Charles E. Atkinson

[57] ABSTRACT

A method, apparatus and procedure whereby a probe, which in the preferred embodiment is a fiber optic catheter, is used in vivo to acquire intra-cellular data from a host. Under computer control, the system detects the specific nature of the host subject's cell kinetic processes. Cells are assumed to always acquire information about their environs and this information is detected and recognized as constituting friendly or unfriendly environments. Using physical analogies, the computer tracks pairing and unpairing of nucleotide sequences as biological radar. A reference analog is used to vary the view of the data-base so that selected portions or subsets of the available analogies lend themselves to sensory presentation from the computer to the user. Provision is made for interactive human communication with the host's metabolism while microscopic resolution and forecasting are obtained. The method and procedure is analog driven and may be embodied in a variety of hardware and software mixes.

38 Claims, 24 Drawing Figures

EXPERIMENT-MACHINE

BACKGROUND OF THE INVENTION

The background of this invention is related to the technology described in an article in the May, 1977 issue of Scientific American titled Cancer Immunology by Lloyd. J. Old. The important technology related to that article involves high powered microscopes and mature clinical medicine methodology used to interpret data retrieved by empirical results of observation and cytological diagnosis by microscopic examination of the cell kinetic of essentially in vitro specimens.

The present invention seeks to extend the capability of that background by using available hardware technology in novel combinations under the control of a novel design architecture that provides the aforementioned background with the ability to capture data not possible before, by radically altering the laboratory setting into an in vivo cytological setting to examine cell kinetics by the introduction of this invention.

An original disclosure document was filed and received by the Patent and Trademark office on Apr. 3, 1978 and that disclosure, document No. 070015 is incorporated herein for reference. Some paragraphs from that disclosure entitled "Communication Theory and Cancer—The Vital Analog" have been included to establish continuity with the data of the original document.

Communication consists of a transfer of information from one concentration through a medium to a joined concentration through a medium. The point where the information originates is called the transmission medium or transmitter and the point where the transfer of information terminates is called the reception medium or the receiver. The most popularly known illustration of this nature is a telephone network. The aim of this concept is to formulate a useful analog for the biological communication network hosted by living organisms whereby a living organism can generate an effective counter against an attack by intruding agents, mobilize its constitutional resources to destroy the development of the attack, and restore the stable balance of good health. When this process fails, the host becomes sick and requires medical intervention to reinforce its natural biological combative mechanisms.

When the attack is non-cancerous traditional clinical practice can readily understand the process and in most cases respond effectively in aiding the host. But if the attack is cancerous, current technology has been at a loss to understand the etiology of carcinogenic processes precisely because these events are unlike other forms of ailments . . . other attacks by "foreign bodies" on a host victim.

With a real time preview of carcinogenic process etiology and development, and the attendant acquisition of "live" data, before the process establishes its roots in the host a complete empirical description of the etiology is provided as it passes through real time domain from incipience to maturity . . . a far reaching empirical theory based on comprehensive experimental evidence.

There are eighteen concepts that form the conceptual basis of this system's architecture. They have been drawn from physical, medical and computer science, but will collectively form, upon amplification, the unified theoretical analytic context within which carcinogenic detection hardware can be built and operated.

1. Simultaneity and concurrently/life supporting protocols.
2. Calibration—The scientific method.
3. Modulation and demodulation/biological versions.
4. Network simulation—driven by real time sensors.
5. Multiplexing.
   a. Time-division.
   b. Frequency-division.
   c. Carcinogenic-time-frame-division.
   d. Parsing a biological data-structure.
6. Transducer sampling rates and machine states.
7. TSR scanning rates and machine states/a variable parsing algorithm.
8. Signal protocols and analog/digital permutating sequences and machine states.
9. Strobing patterns of multiplexing sequences and machine states.
10. Signal decay and communication breakdown and machine states.
11. Network degradation and machine states.
12. Biological communication networks.
13. Biological transponders and modems.
14. Differential detection algorithms.
15. Biological transducers.
16. Data-collection vs. real-time inter-action.
17. Simulation, modelling and data analysis.
18. Interactive simulation and closed loop systems integration.

These 18 concepts must be extrapolated into their biological context to implement this design-architecture; the data acquired must be medically significant and readily available for medical interpretation and intervention. The theory upon which this design rests has a time proven historical antecedent. The architecture of this invention provides upon demand the "yardstick" appropriate to the inter and intra cellular chemistry and the simultaneous interaction of the sensor mechanism to the targeted events in order to guard the integrity of the resulting data.

Hence the need for multi-processing computers that operate separately and concurrently while being an integral part of the design. For every measurement a researcher wishes to make, a plurality of multi-probe systems are required; multi-processing computers are on line to the probing systems and the target process to approximate simultaneity, and a separate system is required to allow the researcher to monitor and control the progress of the computer tracing without interfering with the resource requirements of the experiment.

FIELD OF THE INVENTION

In all of the prior art concerning microscopic diagnosis, a slide is prepared from a tissue culture or from a biological specimen and is examined as a snapshot of an instant of the condition of the host from which the specimen was taken, this examination having no reference to the prior condition of the specimen in a prior instant.

In this invention, a culture or slide is not required since the microscopic examination is made in vivo. The results of prior examinations are used to refine the results of a current examination, using real-time data-bases and communicators.

The summary of the field of the invention tells generally how this is accomplished using state of the art computer methodology to maintain real-time data-bases. In the prior art, real time has referred to the control of the equipment used to create the snapshot of an instant in time, while this invention refers to the real-time domain of the biological process being examined microscopically in vivo.

This invention relates generally to the capture and analysis of data concerning physical and chemical phenomenon in metabolic processes, and more specifically to the method, apparatus and procedure for the application of real-time computers by users of microdiagnostics, in biomedical laboratory environments. This will extend the capability of researchers in the field of biochemistry and molecular biology, as well as others.

This invention is a network system being a method, apparatus, and procedure—MAP—for real-time computer users. The method is the classical experiment-based scientific method adapted to contemporary state of the art sensory probes, connected to contemporary state of the art electronic computers. The apparatus having high speed main and auxilliary mass storage facilities, digital and analog capabilities, data base, large array processing facilities, data communication facilities, pluralities of input and output channels sufficient to support the objective of an experimental context, a generalized graphic-oriented access method for thematic and real-time analytical displays and a parallel logic multiprocessing oriented high level language facility enabling an interactive user-machine systematic conversational interactive mode with a cluster of target metabolic processes. The procedure is to partition the physical spectrum into eight sensory subclasses of operation plus two auxilliary control classes called integration and reference. Each of the subclasses supports a plurality of groups of clusters of arrays of sensors within each subclass, subdividing each subclass into ten narrow band channels. Within each subclass a micro and macro echo ranging focus capability is enabled by executive algorithms in conjunction with the experiment machine firmware and hardware.

The apparatus is used in conjunction with a distribution of clusters of biological computers, controlled by a centrally configured experiment machine central processor, having ten pluralities of mode and pointer registers in groups of ten to correspond to the partitioned physical spectrum operational classification division of the spectrum of acquired experimental data into ten corresponding classes:

1. Inertial
2. Acoustic
3. Ultrasonic
4. Thermodynamic
5. Infra-red
6. Optical
7. Ultraviolet
8. Electromagnetic
9. Integration
10. Reference An object of the invention is to provide a novel virtual experiment apparatus, which incorporates the traditional batch interlude of exchange of information between scientists into the performance context of the ongoing experiment.

Another object of the present invention is to provide for the derivation of a real-time simulation model of the ongoing experiment through a controlling means of an information distribution network.

Another object of the invention is to provide a forecasting means for the same types of experiments performed in the future, derived from the saved results of the same type of experiments in prior applications.

Still another object of the invention is to operationally partition the physical spectrum into a plurality of sub classifications, which in their totality comprise the complete physical spectrum, being the operating spectrum of biological computers.

And still another object of the invention is to provide an automated means, to perform qualitative and quantitative analytical molecular chemical identification algorithms in a real time sensory driven data acquisition apparatus, interacting with host experimental animal(s).

Because the smallest motion at the experiment machine level of data sensing of events that occur within the nucleus of a targeted cell will cause an interruption of the selected data acquisition process, it is required to restore the target directing mechanisms to the position exactly as they were at the instant of interruption within a time interval less than the time required to lose the integrity of a biological record.

In the case of the fibre optic, the means is to move the scan range to follow the motion of the target as detected within the dimensions of the currently active fibre optic cross section; then use the sensor manipulation facility to restore the position of the target process to what it was at the instant of the interruption.

At the same time it is necessary to discriminate between a data acquisition perceived as a relative motion at the sensor host junction and a change in the perceived data acquisition because the targeted process actually went through a cell kinetic progression such as mitosis or an external interference such as an infectious attack.

A simple example is a dividing nucleus followed by a dividing cell such that at one moment a position has one cell and in a later moment the same position has two cells. Using biological computers, the experiment machine discriminates between a relative motion and a chemical process.

The object of multiple data bases and data communication networks is to enable the user to make time critical discrimination decisions at a microscopic level with sufficient accuracy and precision to preserve the real time observation of these processes, as well as to reflect their own networking.

Since the information exchanging algorithms that cells execute are biological in nature the computer that accomplishes this is rightly called a biological computer. In order for such a computer to perform as specified a live host must be connected to it, while operating and translating microscopic events into machine states and computer and network events.

Figure 1:
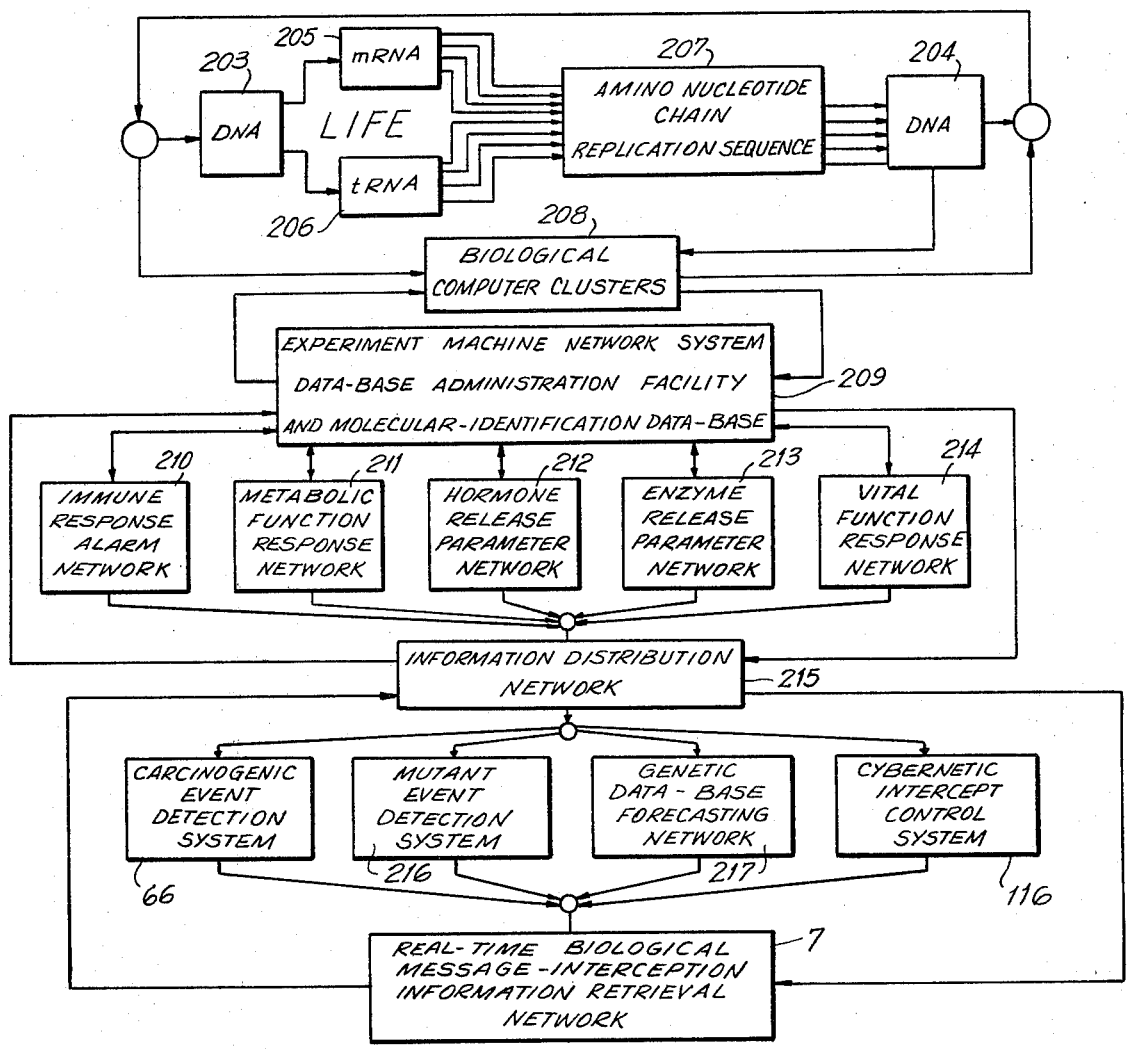
FIG. 1 is a block function diagram of the overall experiment machine network system.

The following references are expressly incorporated by reference herein:

A. Network processing:
 1. U.S. Pat. No. 4,112,425
 2. U.S. Pat. No. 3,309,467
 3. U.S. Pat. No. 4,080,516
 4. U.S. Pat. No. 4,129,864
 5. U.S. Pat. No. 4,101,964
 6. U.S. Pat. No. 4,112,426

B. Platform stabilization:
 1. U.S. Pat. No. 3,982,246
 2. U.S. Pat. No. 4,112,291
 3. U.S. Pat. No. 3,829,659
 4. U.S. Pat. No. 4,104,730
 5. U.S. Pat. No. 4,047,014
 6. U.S. Pat. No. 4,057,708
 7. U.S. Pat. No. 4,034,208
 8. U.S. Pat. No. 4,111,557

C. Biological tissue analysis:
 1. U.S. Pat. No. 4,125,828
 2. U.S. Pat. No. 4,129,854
 3. U.S. Pat. No. 4,111,191
 4. U.S. Pat. No. 4,083,232
 5. U.S. Pat. No. 3,946,361
 6. U.S. Pat. No. 4,094,225
 7. U.S. Pat. No. 4,112,411
 8. U.S. Pat. No. 4,122,518
 9. U.S. Pat. No. 4,135,247
 10. U.S. Pat. No. 4,048,501
 11. U.S. Pat. No. 4,245,646
 12. U.S. Pat. No. 4,181,939

D. Partitioning the physical spectrum and biological data acquisition environments:
 1. U.S. Pat. No. 4,075,883
 2. U.S. Pat. No. 4,172,630
 3. U.S. Pat. No. 4,172,386
 4. U.S. Pat. No. 4,111,050
 5. U.S. Pat. No. 4,096,756

E. Sensor manipulation:
 1. U.S. Pat. No. 4,084,209
 2. U.S. Pat. No. 3,926,040
 3. U.S. Pat. No. 3,982,245
 4. U.S. Pat. No. 3,383,682
 5. U.S. Pat. No. 3,728,519
 6. U.S. Pat. No. 4,112,491
 7. U.S. Pat. No. 4,172,978

F. Sensor group management:
 1. U.S. Pat. No. 3,384,875
 2. U.S. Pat. No. 3,309,509
 3. U.S. Pat. No. 3,697,956

G. Information Theory With Application, pgs. 181–189, by Silviu Gajasu, chap. 10, DNA To Protein Communication Channel.

H. Harvard University Laboratory For Computer Graphics And Spatial Analysis, Computer Mapping in Education, Research and Medicine, 1979, Vol. V, pgs. 79–90, "Computer Graphics in the Interpretations of Cell Kinetics".

I. Textbook of Medical Physiology by Arthur C. Guyton, M.D.

J. Omni magazine, Feb., 1980, pg. 22, "Listening to Life", by Dr. Bernard Dixon.

K. Science Digest Special Edition, Spring, 1980, pg. 34, "Eyes of Medicine", by Claire Warga, pg. 50, "Mind and Body, The Inseparable Link", by John Fried, pg. 84, "Miracles of Microsurgery", by Dina Ingber, pg. 54, "Staggering Proportions", by Malcolm W. Brown.

DETAILED DESCRIPTION OF PREFERRED EMBODIMENT

The sampling rate of biologically calibrated probe transducers are distributed over a range of sampling rates specified using program control, and the response signal rates distributed as the instrumentation interfaces are distributed and stored in core storage of the probe driven computers. A difference in the response of a biological syndrome in a monitored tissue space from the corresponding syndrome being simultaneously monitored in another tissue space by a separate probe may be detected over a range of distributed scanning rates of the probe. The detection mechanism "sampling algorithms" in those vectored areas of probing where differential responses are sensed, respond to take a closer look at the variable which initiated the differential response, and further resolve the relevant variables.

It is known that tissue cell aggregates that are in one state respond and behave differently than tissue cell aggregates which are in different states, and will evince a differing response signal to the duplicate monitoring probe with which each is respectively associated. When variations in the detectability of the differential response vary, scan rate distributions over their defined range of calibration, the internal processing on the channel is saved in digitized code as per its position in the multiplexing protocol.

The means therefore, is to acquire data for analysis of the communication syndromes operative in the part of the body from which it was acquired at the time it was monitored. This communication is responsible for the elusiveness of the operative carcinogenic agents which can entrench themselves undetected before an observer can associate its presence with a cause and effect relationship which might suggest some effective counter measures. This design architecture can effectively intercept this carcinogenic deception.

A user intercepts a biologically induced communication failure, analyzes and describes the modus operandi of the host communication facility involved and then converses with the bio-organic modems whereby communication systems of differing organs communicate with each other.

There are now information conduits available whose dimensions are on the order of the domains of atomic particles, smaller than the domain of cellular composition, such that optic based scanners can resolve these dimensions and extrapolate this data into the logical display required by the operation's human interface requirements.

Other sensors are enhanced by a corresponding association in non-optical bandwidths being so annunciated, each bandwidth having a typical display spectrum.

The real time biological message interception information retrieval network system (RTBMIIRNS) evolves a diagnostic instrument which allows the users to probe the space-time-domain of a tissue space in ten levels of sensing in vivo, as the process continues, and enables the monitoring of the target processes in the precarcinogenic time domain; and as the processes of incipient carcinogenesis take hold, communicate from the system data base areas with parameters indicating weakened biological communications; identify the threshold of incipience, and their development mechanism associated with newly detected parameters. We might anticipate for example, that a biologically generated jamming syndrome broadcasts "chaffing noise", decoy signals, camouflage, or a mix of these to evade detection by the host's foreign body detection network, so that it can infiltrate, ambush, and degrade the host's defenses and finally entrench itself, making the transition from incipience to reality. It is in this precarcinogenic timeframe, before the physical pressures of a tumor makes its presence known, that the host becomes a host to a disease.

Supervisory control and real time simulation monitoring are at the user's command, using the supervisory algorithms component, which allows access to the data base of the real time processes as they occur. As requested information is acquired, it can be retrieved upon request, stored for off line analysis, or/and used to make decisions in the ongoing experiment. There will be pluralities of supervisory consoles, in operation simultaneously. As the onset of a target process becomes apparent using specified differential detection algorithms, the system can be commanded into various tracing simulation modes whereby research priorities are dynamically shuffled to home in on the leading parameters and to converge upon the precipitating, carcinogenic sequences, the life cycle of the host permitting: and also use the data collected to form the vectors for successive supervisory decisions. By this approach, signalling in interesting areas can be subjected to the corresponding scanning and multiplexing procedures, so that the spread over time of the process can also be monitored in the carcinogenic time frame, yielding information as to how the gradient of the spreading is determined within a host.

The multiplexing process separates the signal associated with one transducer point, from others so that a multipoint probing domain corresponding to a user selected multiplexing pattern over a range of sampling rates per transducer point is referenced. The multiplexing spaces between points thus define scanning (strobing) topologies, or span points which define the target area of tissue being probed. The bio-organic parameters to be acquired must therefore depend a great deal on the areas of interest chosen by users. Therefore it is imperative for the users of this system to work under the umbrella of a large scale liaison coordination protocol, to enable the real time handling of the large quantities of data generated.

Dynamically automated real-time chemical-identification algorithms drive the manipulation of parameterized representations of the partitioned physical spectrum, so as to place an associated cluster of biological computers in a combined network status indicative of the real time physical and molecular biochemistry currently in interaction at the point of focus. A real-time trace-observation network results when used interactively with a targeted metabolic biochemical processes.

As datum is acquired from the clusters or sensor/host-junctions coupled to compatible data links through signal paths provided by biological computers, to the experiment machine data-base/data-communication facilities, they are subsequently distributed through a network of user specified experiment machine workstations. Through successive iteration, the precise distribution of information throughout the structural hierarchy of the experiment machine network converges to that of the natural biological communication network of the host animal(s) on which the experiment is being performed.

The invention intercepts critical sequences of a target process conjunctively operating in parallel so as to dynamically adapt topological sizes of the hierarchy of distribution networks to the requirements of the increased rate of data acquisition imposed by new generations of sensors. Each successive use of the experiment machine improves the prediction spectrum over previous uses. The experiment machine becomes a forecasting and testing apparatus for the critical sequences of a target-process embodied in a specific family of hosts, with an actually improved capability each time it is used.

Process control systems in general consist of five constituent functions:
1. Process context—Host environment, physical setting, mechanical stabilization.
2. Acquisition—Capturing the relevant data.
3. Observation—Simulating the process.
4. Validation—Measuring process definitions and calibration.
5. Interaction—Compensatory response resulting in a calibration.

The structure of biological computers reflects the data-acquisition needs in a polymorphous, multi-structural-cell-type target process environment provided by a live test animal, where the complex pre-ordained programmed proliferation of specific differentiated cell-type generations evolves the context of structural and functional cell-type differentiation whereby programmed "chemical re-organization of physical entities continues existence".

Additionally, "biological-radars" germane to the experiment machine architecture, are means of biological computers, and is used in its broadest generic sense to include sonar and other automated "echo ranging"

transducers described herein whereby events are deduced by measuring the observable effects of physical probe sensors implemented with transmission, reflection, detection and analysis of the disclosed sensor-wand probe. The attributes of said probe-wand may occur throughout and within any subclassified subdivision of the physical frequency spectrum that is possible, because of the autoscaling of the sensor-detected-measurement-domains as a built in function of biological computers.

The experiment machine biological computer internal architecture has the ability to react to the perceived attributes of the targeted test environment, deduce the best suited specification of sensor-clustering mapped from the permissible physical spectrum, generate a profile of the best (optimum) sampling sequence, i.e. (real time sensor driven iteration algorithms) for the best optimizations of sensor cluster, as the test environment changes, as is always the case in biological environments, interactively respond by revising the sensor-cluster and repeating the cycle to continuously try to improve and refine the perceived result, as measured and estimated against the initially defined data-acquisition objectives of the target process.

SENSOR SENSITIVITY

As sensors become more sensitive, more elementary events become detectable such that in any given time frame, a greater volume of information is made available in the field of detection. Associated with cell kinetics, a limiting factor has been the lack-of-ability of probes to sense the activity of a cell without disturbing the required normal operating conditions. A cell can lose its nature in the presence of probes which are supposed to sense indicators which will reveal what this nature is.

With respect to normal events that occur within the interior of the nuclear membrane of the cell, the jeopardy is double, since outside perturbations are detected at the surface of the cell membrane, the cytoplasm to the surface of the interior nuclear membrane which then responds, to signal the presence of the external perturbation to the interior of the nuclear membrane, consisting of chromatin, the generic term for DNA. What the response is in the interior of the cell depends on the virility of the interfering perturbation and the intensity of the defensive response. Under natural conditions, other than those subjected to probing human sensors, the response is often to trigger the immume response alarm system that initiates attacks on victim cells, to try to destroy the effects of the perturbations. In some cases, a cellular mutation can take root in the host and thus expand the durability of the mutation. In other cases an infectious disease may result in the host. In still other cases, the offended cell may die.

This invention envolves increasingly sensitive sensors by harnessing the experiment machine in two ways:
1. Bypass the destructive resistance made by the cellular membrane to attempts at sensory measurements;
2. Handle the increased volume of information that results from implementation of increasingly sensitive sensors There are sensors which may be deemed friendly to the suspicious surface of the cell. U.S. Pat. No. 4,111,850, "Organic Photo Conductors and Methods" discloses methods for constructing photo conductive elements on thin, semi-transparent, flexible substrate for use in many areas such as light sensitive switching functions, the photo conductors being applied from solution or suspension in a fast drying liquid on to an electrode assembly attached to a flexible plastic substrate. The conditioning of such derivative photo conductive sensors with attributes deemed not hostile by a target cell implements the destructive resistance bypass. The sensor will have properties that are specifically characteristic of the host metabolism being used. Incorporating into a sensor the blood-type, genetic profile and other essentially host specific metabolic properties and the metabolic profile of the targeted cell type.

Operating a biological computer being driven by the sensors that are attached to it, the biological computer state in any given instant is a reflection of the state of the pertaining operating sensors. The sequential states of the biological computer is an "image" of the living sequential states of the subjected cells, and their interaction.

With regard to cell geometry, size is an important constraint, since sensor sensitivity is relative to the scale of measurements and the time frame in which the measurements are made. As a cell metabolically progresses through its life cycle and all of the attendant changes associated with this cycle, then there is an interactive need to change the sensors that are being used so that they will be appropriate with respect to scale, time domain, and friendliness, for the current state of the cell in its metabolic progression.

The biological computer dynamically activates sensors as they are required. In the course of operation, records are taken of this status while sensor clusters are dynamically reconfigured to best fit the sensory data acquisition junction of the current trend of the progression.

SENSOR CLUSTERS

The positioning of sensors associated to specific sub-channels relate to the technique of relative scale. A relative motion of one one-thousandth of a millimeter, when viewing a sample under a microscope will result in a shift of the field of view across many numbers of structures which are the objective of the view. The shifting of the field-of-view is a real-time event.

Many pluralities of cell-types will be in the field-of-view as a consequence of the complexity of the host organism's constitution and the random and sporadic motions caused by interaction between the sensors and the sensor-host-junction. This invention transmits the occurrance of a shifting of the field of view to the controlling biological computer. The optical fibre transmission system such as described in U.S. Pat. No. 4,112,293, "Optical fibre data transmission system", provides a means of transporting the effect of a host motion interacting with a sensor junction motion to an analytical station such as that described in U.S. Pat. No. 4,112,295, "Apparatus for direct measurement of displacements with a holographic scale".

An optical-fibre sensor is partitioned to carry detected variations of light frequencies in various partitions of the fibre cable. An interaction between the associated sensor and the sensor-host-junction resulting in a shifting of the field, is detected in an analytical station by controlling changes in the representative signals, conveyed through the optical fibre catheter. The optical fibre transmission system has a transmission cross-sectional area as small as the radius of the cell substructure targeted.

The biological computer includes sensor clustering in the videoband which has associated analog in other pluralities of sensor classification groups. The algorithms (to detect and transmit representative signals, of occurrences of shifting fields of view with respect to the associated sensor group class operable at the instant-of-shift) are staged for transmission to a biological computer data base. The multiplexing patterns selected to facilitate sensor clustering is a user responsibility, aided by the data base. The dynamic iteration of selected multiplexing patterns used in controlling the scanning procedure of the various sensor group classifications is the resource controlling the facility to stabilize the target space of the experiment and implements the facility to detect the chemical states coincident with the target space selected. The shifting of the field over a time-span is captured by high speed computerized recording to a data base as are the stabilization-parameters and the chemical state parameters. Successive iterations of the controlling biological computer processor cycles will seek to maintain the aiming and focusing of the sensor groups in the selected multiplexing sequences in accordance with the commands of the user relating to the selected target space. Such means are provided in the biological computer's biological radar facilities. Lloyd J. Old's experiment:

The DNA experiment in batch mode is how the experiment was carried out in the past.

1. Carcinogen is injected under the skin of a selected specimen. The application of the carcinogen with respect to cells is not a controlled process. The general location is known, but the cells involved are not; see FIG. 2.
2. Several days to several months expire until a tumor is observed. Conventional tests are made as scheduled to log clinical data. The tumor is surgically removed and after a period of healing, malignant cells from the removed tumor are reintroduced into the selected specimen, and a control specimen not previously exposed. When the selected specimen proceeds to a specified degree of inbredness a successful resistance to the reimplantation of tumor cells is made. Less inbred specimens have shown weaker displays of resistance.
3. The latest techniques of biopsies, modern biochemical analysis, highly resolved micrographs derived from real time sem's are used to draw conclusions in preparation for the next set of experiments. Knowledge is advanced by varying the selection of specimens to cover a spectrum of genetic characterizations and carcinogens, producing an encyclopedia of empirical results, a new volume being added each year, each laboratory introducing improvements, sharing the results, refining the tools and material used, increasing the sensitivity of their experimental procedures.
4. Experiments are now done in what is fundamentally known as batch mode, as opposed to the interactive real time mode; as technology advances and pressures mount to increase the return of knowledge and profit units per research dollar invested, the conversion from the batch mode to the interactive real time mode is being made.

Figure 2:
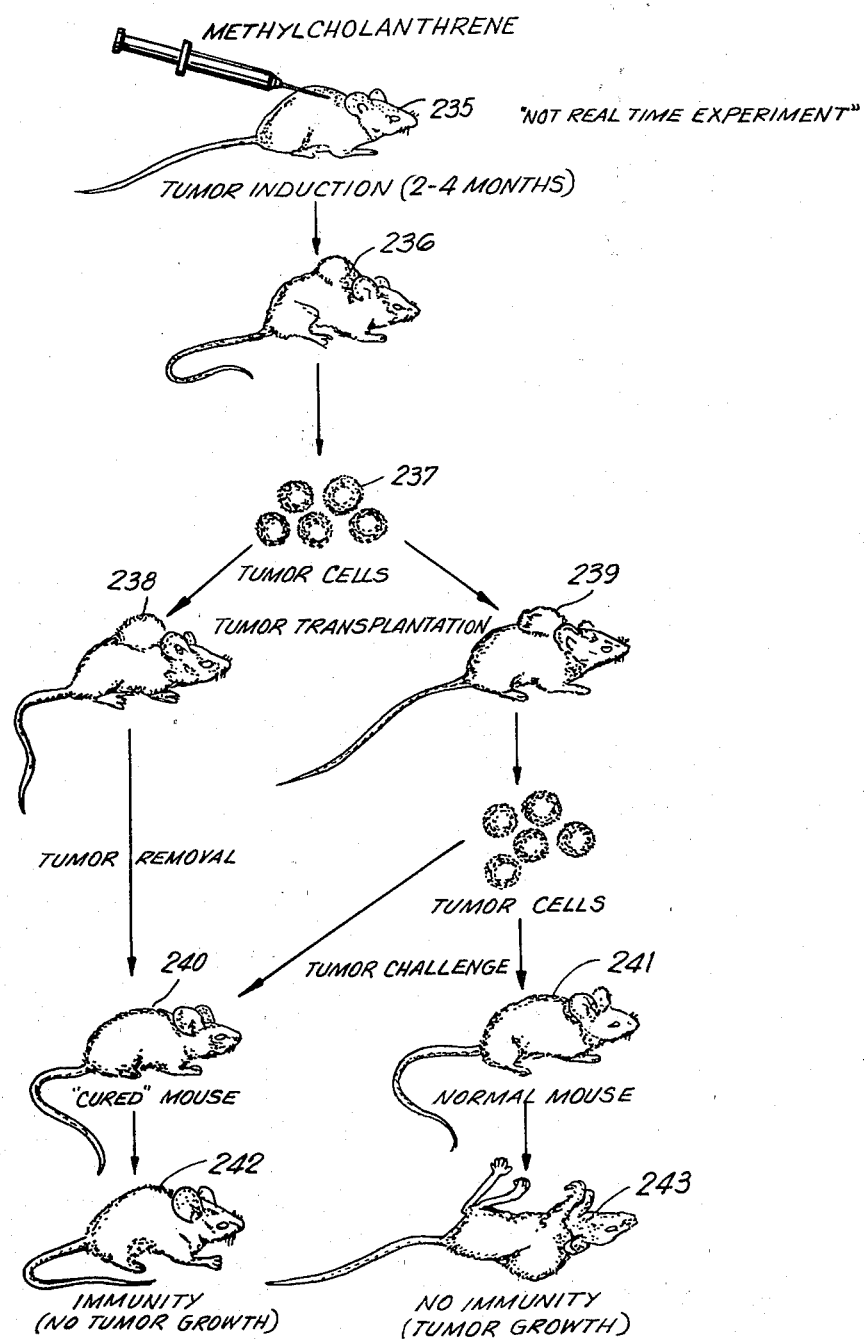
FIG. 2 depicts live mouse population of classical immunology experiment.

Referring now to FIG. 2, "Immunity to chemically induced tumors can be demonstrated in mice. Tumors appear two to four months after an injection of methycholanthrene under the skin. Cells from the induced tumor can then be successfully transplanted to other mice of the same inbred strain. If the tumor is removed from a recipient mouse, that mouse will be resistant to subsequent injections of cells from the same tumor. Tumor cells injected into a normal mouse of the same strain, however, will proliferate and kill it." Data-base facility for acquired data partitioning:

1. The segments of the different data-base are:
   A. Normal segments
   B. Abnormal segments
   C. Carcinogenic segments
   D. System control segments The procedure provides for multiple populations of experimental specimens and pluralities of carcinogens to be recorded so that ever increasing numbers of early warning alarm sequences can produce more accurate, precise and comprehensive results, the more frequently the experiment machine is used in a broadened time spectrum.

Sensor groups are selected and installed into the biological computer cluster.

A population of selected experimental specimens are put in place as required. The monitoring sensors are turned on. The real time experiment data base administrator initializes the files with the experiment's required start up initialization data, as provided by the selected sensors and specimen and other constraints researchers might wish to impose.

The cells and tissue space are selected from the experimental population using operating microscopes in conjunction with biological computers with supporting hardware and procedures. The carcinogens are applied using microsurgical procedure, varying the strength of the carcinogens providing a dynamic spectrum of significant distribution over a population as well as the capacity to generate critical sequences for comparative analysis in bold relief.

As the experiment proceeds, the data bases become populated with live data segments immediately available for inspection and analysis, throughout a network of surveillance and interaction stations. Now participation in the experiment interaction or intervention is possible on a scale thus far not achieved.

The data generated in a current experiment becomes a part of the start up data base of future experiments, in connection with related host animals. Significant events not presently visible are detectable and observable through comparative algorithms and highly sensitive data filtration operations. The breach caused by batch mode interludes is no longer a consideration. The real time DNA experiment using the procedure to implement the primary embodiment of this invention.

1. Connect all interfaces from real time experiment sensors to real time experiment data base generator interface connector frame. The frame is connected to a distributive processing computer network using special data links and special hardware.
2. Measure the degree of invariance and the pertubation of invariance caused by imposing "foreign influences" on replication and related genetic mechanisms, or that caused by selective breeding procedures. The immune system is a prime candidate for the area of focus.
3. Incorporate the data acquired in steps 1 and 2, into the "families" genetic data base, use this to obtain an increasingly sensitive and improved diagnostic procedure to identify the presence of foreign substances. The legacy of each generation to the next will be an improved diagnostic capability because of the additional "knowledge" provided to the genetic data base of the next generation.

The following steps outline the new method:
1. Algorithms are implemented dynamically to optimize the use of the sensors as required. The end user laboratory specified its command interface requirements for customized software interfacing depending on the changing display needs of the experiment.
2. The traditional batch interlude required by the exchange of information involved in the experimental study is pre-empted since it is a requirement that participants must coordinate in a radar workstation network to handle the increased volume of data that is generated.

Referring now to FIG. 1, 203 is a simplistic representation of the essence of the metabolic target process which is dealt with in great detail by three of the additional references specified elsewhere, namely:
(1) "Cell Kinetics" by Messrs. Shackney & Lincoln
(2) DNA to Protein Communication Channel by Giasou
(3) Physiology by Samuel Guyton In the course of cell division the DNA in the nucleus of a dividing cell performs a complimentary unpairing into mRNA 205 and tRNA 206, each using a characteristic sequence of a permuted combination of the four known base nucleotides to implement the host-specific combinant sequence for that cell type to facilitate 207, the amino nucleotide chain replication sequence, manufacturing the needed proteins and derivitive products to form 204, which is the resulting DNA distribution of two daughter cells, each being of the same type as parent cell 203. Biological computer clusters 208 represent various pluralities of computer controlled data acquisition sensors connected in vivo to a live host subject(s) that are supported on an experiment machine platform stabilization system, that operate conjunctively to distribute data to experiment machine network system 209 which comprises essential controls that provide the means of administrating a set of data bases resulting in the real time identification of the molecules and substances that comprise the life process as it occurs in target cells 86, 87 and 88.

Experiment machine network system 209 facilitates the passing of such information to subsidiary networks 210, 211, 212, 213 and 214 in accordance with a user defined interface protocol that specifies the attributes of a molecular structure for a given cell type as they pertain to be respective networks, immune response, alarm, metabolic function, response, hormone release parameters, enzyme release parameter and vital function response, within the time constraints of a current probe interval. Other network types may be added by the user within the framework of this invention. Observations of these types of events are exchanged with 209 which can notify controlling operators of 208 of such needed feedback information to preserve the integrity of future probe-interval operations. Information distribution network 215, is comprised of block 66, 116, 216, and 217 which collectively comprise real time biological message interception information retrieval network 7. The system 66, 216 and 116 are inclusively real time computers with data-base and data communication in addition to close physical association with 208 and 209, while 210, 211, 212, 213, 214, 215, 216, 217 and 7 are networks of types described that are organized to conform with the desired information distribution protocol prescribed by the users requirements.

BIOLOGICAL COMPUTER

The following consists of an outline format related to the preferred embodiment, followed by a description of functional components, and their relevance to each other.

I. Complete partitioning of physical spectrum.
  A. Plurality of classes of subdivided sensor groups.
    1. Mechanical
    2. Sonic
    3. Ultrasonic
    4. Infrared
    5. Visible
    6. Ultraviolet
    7. Thermal
    8. Electromagnetic
    9. Integration sensor
    10. Reference sensor
  B. Plurality of class of channels to support multiple levels of channel divisions (banding) for each class of sensor group specified in A.

II. Multiple point probing.

III. Isolation of probing bit stream on a subdivided class basis with respect to sub-classified sensor group arrays.

IV. Vernier-type refinement of target selection process with respect to II and III, specifying modification algorithms required for evolving more sensitive sensor matrices.

V. Concentration of bit streams for each sensor group for multiplexing and networking algorithms.

VI. Demodulation of V for complete input/output control and analysis.

VII. Distribution and control of information resulting from I to VI to impose human intervention.

Figure 17:
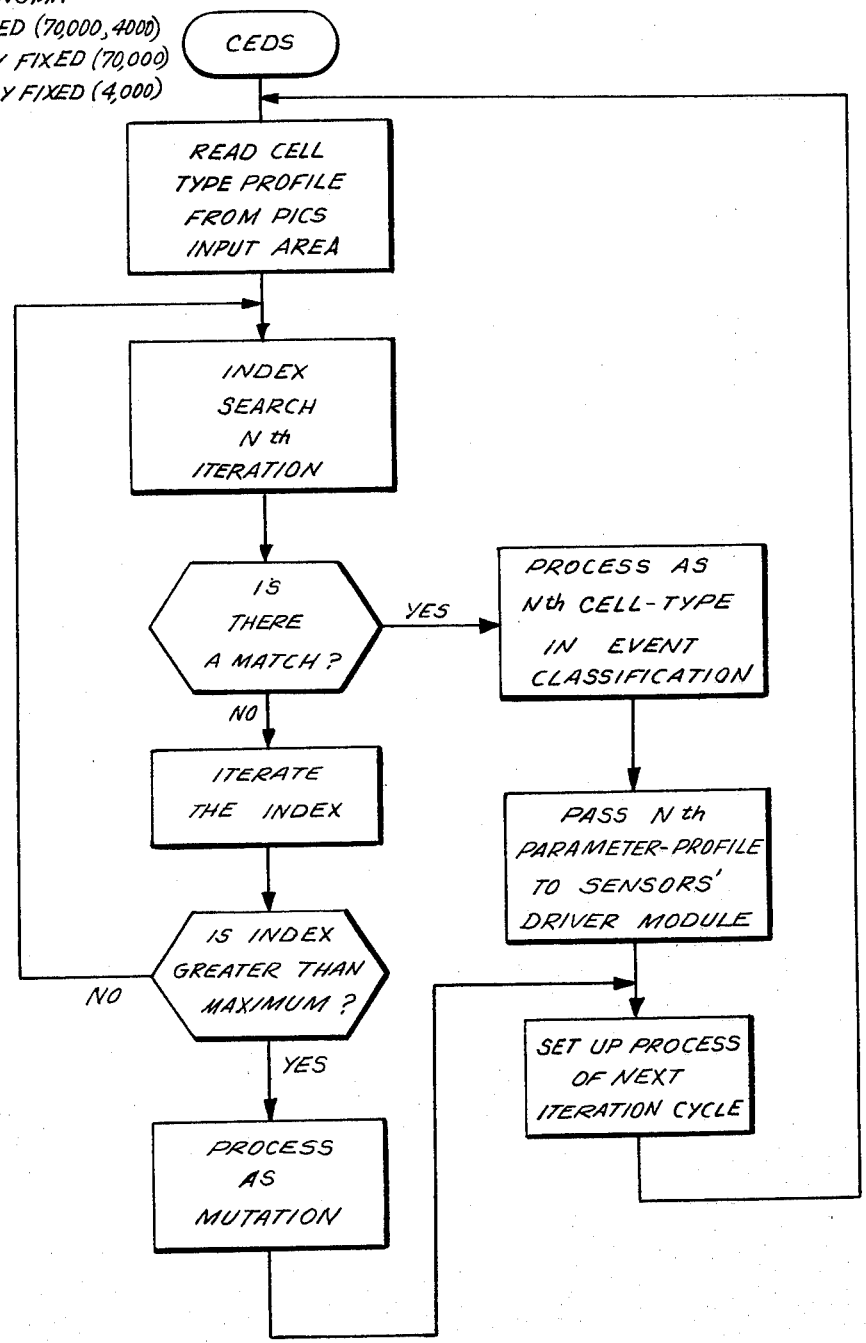
FIG. 17 is a flow chart of the experiment machine operation guidance logic.

VIII. Proliferation of classes of cells definitions with respect to host programmed differentiation.
  A. Main class
    1. Structure
    2. Composition
    3. Association
    4. Function
  B. Sub-classification
    1. Structure
    3. Composition
    3. Association
    4. Function
  C. Proliferation sub classification of an element in B.
    1. Structure
    2. Composition
    3. Association
    4. Function
  D. Infra-structure of cell.
    1. Membrane—primary and nuclear
    2. Cytoplasm—composition and classification
    3. Interior of nucleolus—DNA
    4. Transport mechanisms with respect to class
    5. Life cycle between mitosis
    6. Orderly termination and replacement of cell
  E. Principles of interaction between and among cell types with respect to classification algorithm, see FIGS. 17 and 18
    1. Tissue definition
      a. automated cell type selection b. biological radar to allow human interaction with life process in a real time mode on line
c. aiming of experiment machine into target space-experiment machine stabilization system and biological radar
2. Live host experimental context
   a. Calibrate experiment machine with experiment, control and calibration group(s)
   b. Select target for experiment
   c. Administer carcinogen to experiment population
   d. Track and victim cells of carcinogenic attack
   e. Build genetic data base update for host experiment group
   f. Perform real time analysis to generate pluralities of forecasting models

FULL DUPLEX INTERACTIVE GRAPHIC DISPLAY AND NATIVE LANGUAGE facility;

With the varieties of sequences of chemical and physical states that arise in metabolic processes are the real time constraints. As sensor groups become more precise in reporting selected target space on a real time schedule the consequence will be the simultaneous operation of a plurality of collections of sets of sensor group arrays, each set consisting of ten groups generating a volume of biological records far in excess of what an individual or group could handle in less than a network of workstations.

A centralized communication monitoring facility receives a copy of all events reported. This same facility schedules the routing of the biological records, throughout the information distribution network. As a result of this means a global view of the activity of the information distribution network is a simulated real time operating model of the target space to which the biological computers are connected. The real time interaction capability of the experiment machine network with the host controls data base, data communications resources as an integrated facility, and distributes segments of biological records to users based on a selected hierarchical protocol that corresponds to the structure of the target space.

BIOLOGICAL COMPUTER MACHINE STATE DEFINITION

The chemical composition of a substance becomes known whether it be inorganic or organic by making qualitative and quantitative sensory evaluations and measurements of physical indicators scaled to the requirements of the dimensions of the sample of the substance, using data bases and network communicators.

In cell kinetics the chemical composition targeted is an ongoing dynamic process whereby sequences of chemical composition targeted is an ongoing dynamic process whereby sequences of chemical reactions interactively occur in parallel with and in the domain of electrolytic ambiences, to form the chemical composition of cells and organs, in a given time frame.

In order for two different biochemical states to be possible, there must be a unique set of qualitative evaluations and quantitative measurements, for which no duplicate set exists save for an identical chemical state; and the two sets will differ in at least one physical feature . . . such that two differing chemical states can be repeatedly identified as differing.

A biocomputer has at least one sensor group for each of the known senses. A biocomputer is in a unique machine state for each different metabolic event its sensors detect. Thus a machine state is a topological map in the mathematical sense of the physical and chemical events emanating from the target-space.

As physical bit-streams are parsed into biological record segments as they are time stamped and written into the data-base storage facilities. This is done for each sensor group. A single biological record is then composed by concatenating the respective segments of each sensor group . . . bearing the same time stamp. In the formation of one biological record, a time stamp will occur ten times, but may be compressed using known data-base methodology.

| F1 | F2 | F3 | F4 | F5 | F6 | F10 |
|---|---|---|---|---|---|---|
| TS1 | TS2 | TS3 | TS4 | TS5 | TS6 . . . | TS10 |

The bit streams between time stamps may or may not be of the same length and the time stamp shown as TS10 in the above record layout may be the time stamp of the previous biological record as these records are generated they are captured according to their current interest. The primary function of such biological records is for the real time comparison to corresponding (having the same time stamp) biological record of a second biological computer which is sensored to a different position for reference or testing. In the most general case there will be many such operating biological computers.

The order in which the sensor-group bit-streams are placed in their segments are of significance when comparing different biological records. In order for two biological records to be considered identical their composing bit-stream fields must have been concatenated into the record in the same order with respect to the sensor groups from which the bit-streams were derived. Thus, if at a given instant of time two biological records produced by two biocomputers are found to be identical then the machines are in identical machine states.

Assuming that two computers are sensored to the same host then when they are found to be in the same state it is assumed that the field-of-view of the probe are occupied by the same cell or cell-structure type. If they are in differing states then the opposite is true. The process by which two biocomputers are iterated into the same machine state is calibration. The sequence of records that is generated populates the data base for the cell-type that characterizes the current target space and is used to refine future measurements of the same cell type in this host.

Future cells related to this current target cell will have the same genetic specificity integrated into their records. The measure of invariance of genetic specificity with respect to bredness can now be made, with future measurements improved by using prior measurements from the data base.

Figure 3:
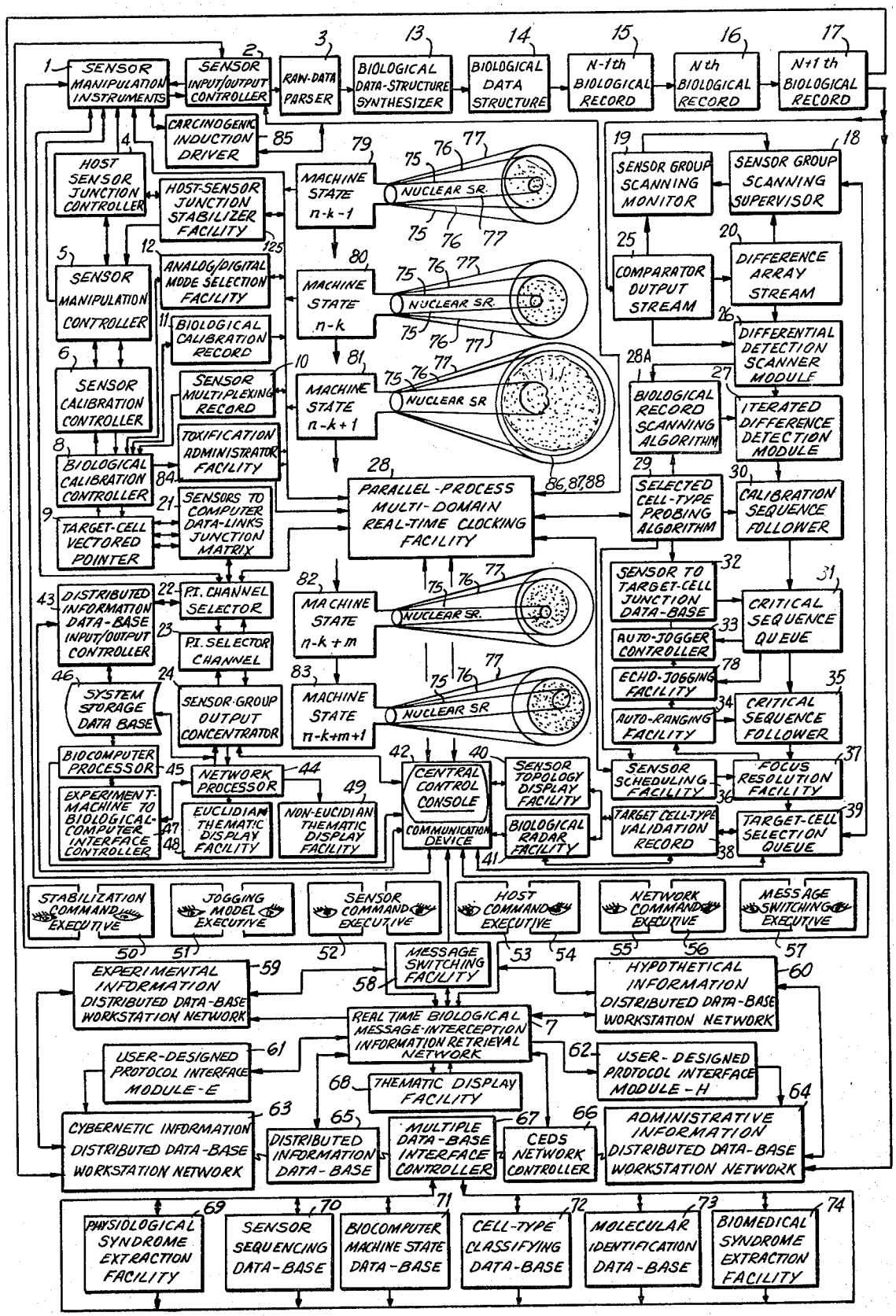
FIG. 3 is a function block diagram of internal operations of the experiment machine system.

Referring now to FIG. 3 the sensor manipulation instruments receive input commands from real time biological message interception information retrieval network 7, host sensor junction controller 4, central console 42, probe interrupt channel selector 22, parallel process multidomain real time clocking facility 28, and when the cancer experiment is in flight from carcinogenic induction driver 85, and from toxification administrator facility 84 which transfers its commands indirectly using the parallel process multidomain real time clocking facility 28, which in general is a general purpose real-time computer used as a means to centralize and concentrate and dispatch time critical commands and command decisions to the remote but related components of this network system. Sensor manipulation instruments 1, exchanges information with sensor input/output controller 2 receiving commands to cause a change in a specific band as defined in FIG. 9, with respect to probe interrupt channel selector 22 and acknowledging to 2 that the commands have been carried out by the appropriate transmittance of information. The nature of the manipulation is done 1 is to aim the sensors of all the bands in accordance with the commands received, such that the appropriate transmittance of information means is a data stream characteristic with the group of bands selected for the time interval controlled by 22 and 23, which is the probe interval referred to in FIG. 1.

The host sensor junction stabilizer facility 125 gathers the information it needs from the host sensor junction controller 4 and 28, the successive machine states iterations 79, 80, 81, 82 and 83 to track a target cell(s) having a scan range shown as 75, 76 and 77, and keeping the selected target 86, 87 and 88 in the selected field of view that prevails for a current interval defined by the operation of 22. Platform system 125 sends commands to 5 which goes through a command exchange sequence with 4 under the supervision of 125, it being understood that 42 is the source of origin of command and information because of its rapid access to data base information shown as 69, 70, 71, 72, 73 and 74.

Because of a probe-interval change, a sensor multiplexing record 10 is generated that conforms to the operation of 22 and is used to interact with the sensor sequencing data base 70.

As the metabolism of a selected target space progresses, the sensor multiplexing record 10 changes and this is reflected in the biocomputer machine state database 71.

To select a target, console 42 solicits information from 59, 60, 63 and 64 using 7 and 53 after receiving the correct information which originates from data bases 69 through 74 controlled by 59, 60, 63 and 64 under the umbrella coordination of 7. As a result of this rapid access to always current real time data base information facilitated by 65, 66, and 67, the thematic display facility 68 is understood to mean a biological radar display set of the type shown in FIG. 9, and is in general use whenever a workstation network is shown such as 59, 60, 63, 64, 40, 48, and 49 in accordance with description of biological radar facility 41 as a specific component of the cybernetic intercept control system shown as flow charts in FIGS. 16 through 24 inclusive.

When a target tissue space is to be selected, console 42 coordinates correspondences between the executives 50, 51, 52, 53, 54, 55, 56, and 57 which may be manual or automatic depending on the type of jogging 93, the required information is retrieved from a data base and the necessary data base space is initialized for real time interaction; the supporting message being distributed throughout the workstation networks of data bases 65 and networks 66 using 44 through 48 and 49, 40 and 41 using 42; accordingly the target cell's vectored pointer 9 is initialized with the cell type profile data from the cell type classification data base 72 and 73 transferred to system data base 46 for expediting and initializes target cell selection queue 39, where it is used as a baseline to evaluate currently referenced cell type data according to partitioning of the physical spectrum by 22. The target cell selection queue 39 has the definitions of three cell types 86, 87, and 88 as does 9. The sensor scheduling facility 36 uses the multidomain timing capacity of 28 to allocate the scanning resources for retrieval of vital information regarding calibration, control, and experimentally models 86, 87, 88. The target cell type validation record 38 receives the live data resulting from pics 22, and cybernetic intercept control system 116, scanning with correspondence to the 86, 87, 88 experiment models and compares these values with the baseline in 39. The selected cell probing algorithm 29 consists of information from data bases 69 through 74, the operation of 22 under control of cics 116, in direct response to commands received from sensor scheduling facility 36, which reflects commands it receives using console 42, handling executive commands from 50 through 57. As biological records 15, 16, 17 are received from controller 4, as a result of the operation of biological scanning algorithm 28a, it is understood that information received here is made simultaneously available to 43 and 67 such that the current real time information bubbles into 7 and ultimately the networks 59, 60, 63, and 64 using 65 and 66 within the current probe interval.

As algorithm 28a operates receiving information from 26 and 29 it compares the current iterated scan of cells 86, with 87 and 88; then builds the output to the iterated difference detection module 27; to the calibration sequence follower 30 which itelf has been alerted by algorithm 29 on the type of information to pass to the critical sequence queue 31 and junction data base 32 which contains relative motion parameters regarding host sensor junction topology as well as molecular identification information relating to cell type probing algorithm 29. This information is bubbled from 32 to 43, 44, 46, 47 and ultimately to 7.

In response to what is bubbled out into 7, commands are issued and routed back to 32 and to 1 to make corrections so as to achieve the required comparison in the probe interval between 86, 87 and 88. As sensor manipulation sequence 1, 2, 4, 5, 6, 8, 9, 10, 21 and the 125 sequence for stabilization takes place, scanning supervisor 18 continues the operation of algorithm 29 by retrieving current images of cells 86, 87 and 88 comparisons from the sensor group scanning monitor. The comparator output stream 25 is understood to originate from detector module 26 repeatedly in the selected interval fed by iterator 27, which having received instruction from algorithm 28, passes the refreshed comparison results of 86, 87, and 88 to the current interval to 30, 31 which are passive until instructed but pass images of information they receive to 33, 78, and 35 which sends a current image of its operation to focus resolution facility 37.

As a result of this continuous operation the disciplined commanding of the sensor manipulation instruments, host sensor junction stabilizer facility and the data bases in coordination with 7, an interval will be found where the current segments of 86, 87 and 88 will compare equal and at this time the system will be in a calibration state. True images of the three cell types chosen will be annunciated at workstations of 7 to represent the cell type of substructure targeted and known to be in a position in the field of view of the selected bands of the associated sensor groups for the current probing interval. In order to continue with an experiment, the target bearing portion of the system is locked into this calibration state for the given selected cell type probing algorithm, again upon command from console 42 as a result of coordinating the activities of executives 50 through 57. At this time in the scanning auto jogging controller 33, echo jogging facility 78, the auto ranging facility 34, the critical sequence follower 35, the critical sequence queue 31, and sensor to target cell junction data base 32 operate to preserve the aim status the system is in when the lock on target command is given. If a relative motion at host sensor junction 127 is determined to have taken place, an image of the motion is bubbled into 31, 32 and 35 using the operation of 33, 34 and 78, and commands are generated to cause the inverse relative motion to occur in an interrupting cycle of the scan to neutralize the effect of the initiating relative motion.

For a given cell type of known metabolic phase with a known nuclear state, a range of relative motion within the scan range of a given probe interval may be commanded to be acceptable for current user purposes, thus providing the use of random relative motions to be a means of additional scanning to yield biological records indicative of the environs surrounding the selected scan range of the locked-on-target space.

Referring now to FIG. 4, 130 through 139 are the partitioned domains of the physical spectrum described in FIG. 9, 130a through 139a are the subdivided narrow band inner channels of each domain of the physical spectrum which provides for the bidirectional start stop signal recognition capability of the probe interrupt channel selector, needed to discriminate a variety of levels of intra-cellular transition state changes, for pluralities of cell types. These cells 86, 87, 88 are shown being injected by carcinogenic induction driver 85, which corresponds to the injection given to laboratory mouse 235 shown in FIG. 2 in intent only, since the experiment machine network system 218 provides a radically altered laboratory setting.

Numerals 130 through 137 and 130a through 137a are especially familiar in the fields of physical science as the types of sensory experience we can observe using different combinations of our perceptual apparatus depending on the initiating phenomena. 138, 138a, 139, and 139a are different generically as they are more concerned with the memory and ordering of sensory phenomena. The means to remember are provided by the data-base facilities of the biological computer 202, which receives from cybernetic intercept control system 116 chronologically ordered real-time images of sensory data which is archived to its data-base resources on commands received from 128. Likewise, images of prior data is reproduced from data-base resources on commands received from 218 or 202. Then using biological record data base intercept processors 99 and 100, data images are sent to a designated bioradar workstation 41 for real-time annunciation of the sensory data signifying the currently targeted cells.

Integration band 139 and composite narrow bands 139a are shown connecting to the experiment machine partitioned domain physical spectrum multiplexer 221, which is data-link connected to code leveller and biological record synthesizer I/O buffer 171, which is likewise linked to pics echo burst receiver multiplexer concentrator 170, being the path along which the acquired target cell data begins its journey through the experiment machine network system, 218. This operation has been shown in FIGS. 14, 13 and 3; and called probe interrupt selector channel, 23 and should be understood in either case to belong to the same, the means of creating an information channel specific to a targeted cell type. It should also be understood that although three target cells are shown to be connected to what are apparently different aspects of this invention, these connections are time dependent and that each targeted cell is subjected to all aspects shown in the drawing. Specific details on how this is accomplished are described in other figures and flow charts shown in FIGS. 16 through 24.

PLATFORM STABILIZATION

The multiplexing patterns selected to facilitate sensor clustering is a responsibility assigned to the user. The dynamic iteration of selected multiplexing patterns used in controlling the scanning procedure of the various sensor group classifications is a means of controlling the facility to stabilize the target-space of the experiment and controlling the facility to detect the chemical states coincident with and attendant to the said target space selected. The shifting-of-the-field over a time span is captured by high speed computerized recording as are the stabilization parameters and the chemical state parameters. Successive iterations of the controlling biological computer processor cycles will seek to maintain the aiming of the sensor groups in the selected multiplexing patterns in accordance with the commands of the user relating to the selected target space. Such means are provided in the biological computer's biological radar facilities shown in blocked relative logical positions in FIGS. 8, 13, and 4. Computer command language allows the user to select and change iteration patterns and multiplexing sequences, to dynamically inquire into the status of said selections and sequences, to select and set required parameters relating to target space selection and experiment-platform stabilization parameters and their sequencing, see FIGS. 18, 19 and 20 to command, control and inquire into the parameters and their associated status of the biological radar facilities of the biological computer, to cross-reference all of the facilities provided by the biological chemistry data base, physical chemistry data base, and derivitive data bases and to enable an interactive communication between a plurality of a hierarchy of subclassified data bases with a network of experiment machine workstations and to interactively communicate with the language facility itself to dynamically implement new sequences and to redefine, manipulate, parse, convert, convolute or otherwise compute or in any graphic fashion interact with biological records acquired by the biological computer so as to be able to respond with compensating operators which allow the user to dynamically interact in a conversational mode on a real time basis with the metabolic process.

Since the complex host embodies thousands, perhaps millions of related, synchronized and otherwise coordinated subsidiary processes constituting the metabolic environment in which the biological computer must operate in a real time mode, there is a corresponding plurality of workstations to report the events of the number of the related constituent subsidiary processes on an as occurs basis; when an event occurs, a report of it is routed to a specific workstation where a user biological radar set operator indicates with an input sequence entered at the workstation data entry facility, what the event is, and supporting sequences required by protocol.

By selectively multiplexing the operation of the array sensor matrices of the associated biocomputers, to select those combination of sensors that keep the calibrated operation of biocomputers in sequentially identical machine states with respect to given position, over an extent of tissue, then the sequence of machine states generated is a "record" of the cell(s) located at and occupying the targeted positions. The length of time that this is true is a measure of the stabilization of the experiment machine environment.

Figure 5:
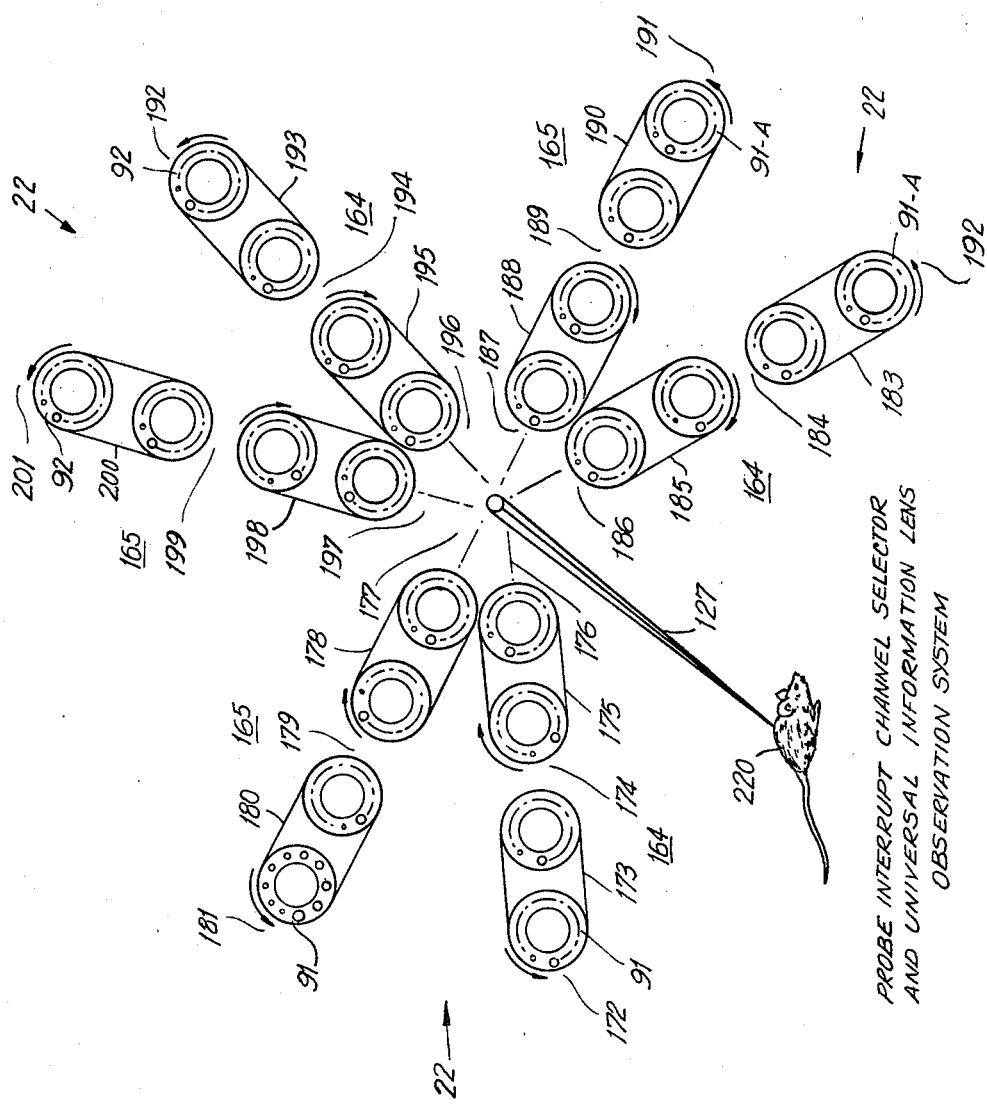
FIG. 5 is a function diagram of the probe interrupt channel selector.
Figure 9:
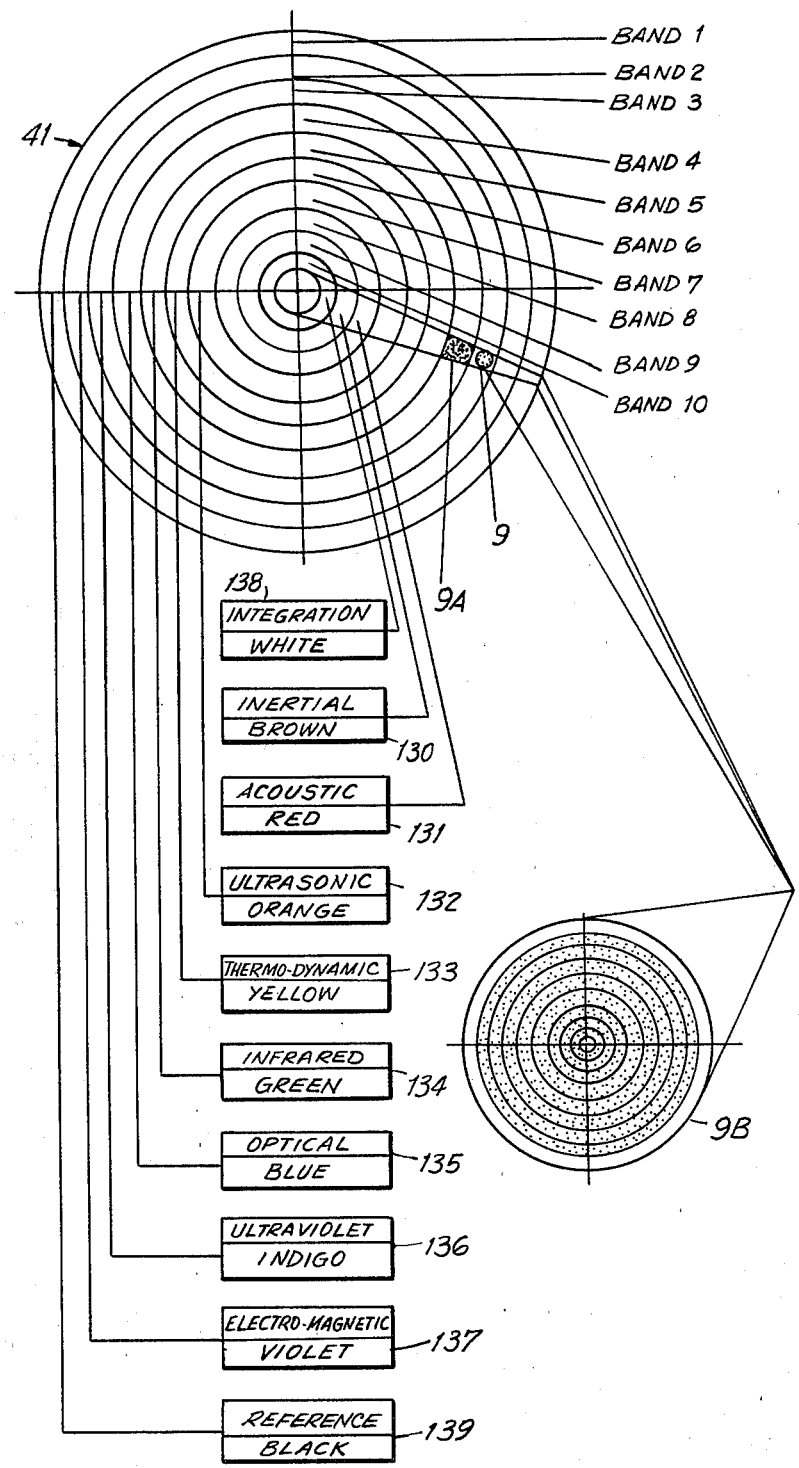
FIG. 9 is a function block diagram of biological radar topology related to the physical spectrum.
Figure 10:
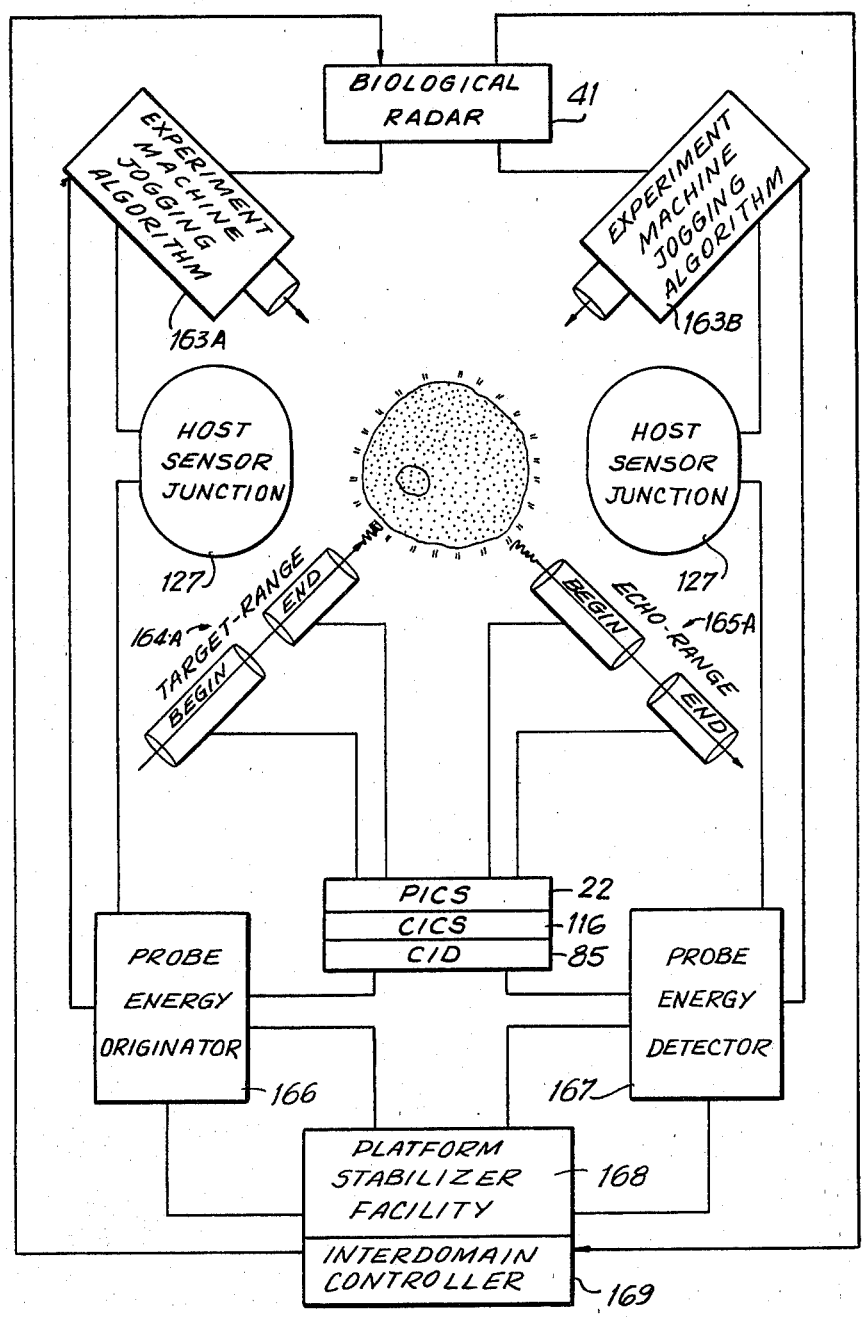
FIG. 10 is a function block diagram of the biological computer element prototype.
Figure 11:
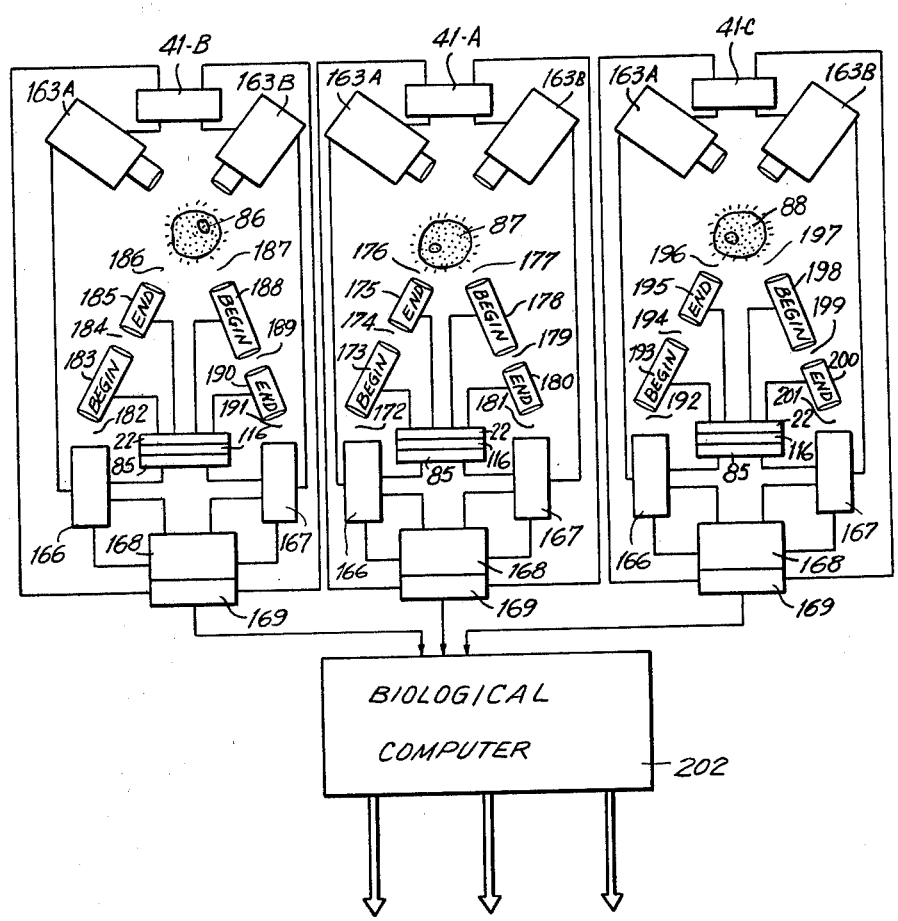
FIG. 11 is a function block diagram of the biological computer prototype.
Figure 24:
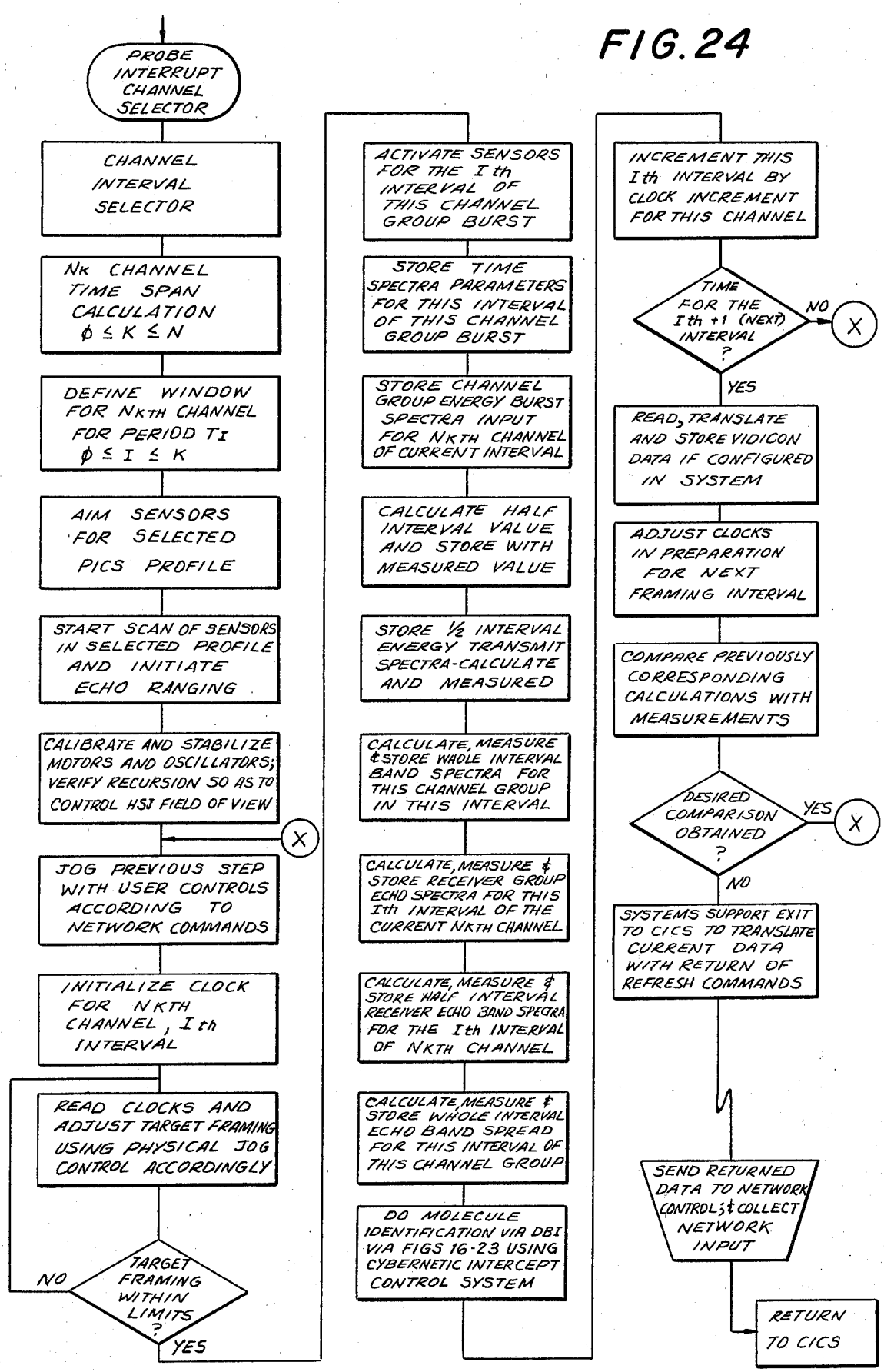
FIG. 24 is a flow chart of the probe interrupt channel selector.

Referring now to FIG. 5 a host subject 220 is shown having a host sensor junction 127 with the three interactive elements of the experiment machine network controlled probing operator 91, 91a and 92, calibration, control and experimental models. 172 through 201 have been defined in the description of FIG. 11. 164 and 165 have been described in the detailed description of FIG. 10 and are shown here to be for 164 the collective sets of 172 through 176, 182 through 186, 192 through 196, also called the target range; and for 165, the collective sets of 177 through 181, 187 through 191, and 197 through 201 also called the echo range for each of the three network operators. The models 91, 91a and 92 in this figure point to the concentric array of circles that are not numbered individually but represent the physical information paths corresponding to the partitioning of the physical spectrum shown in FIGS. 13 and 9. They may include multiple circles within one band to permit an associated hue spectrum with up to ten subdivisions for one partition of the spectrum which is the means for mapping one sensor-group array of transducers, 89 and 92 to represent the association with the currently operable permuted combination of sensor-group arrays of pics 22 in the current probe interval. A flow chart of 22 is shown in FIG. 24.

In addition each half-cylinder corresponds to the time-of-flight duration of the information for which it is the channel and is related to the natural characteristics of the domain of which it is a member such as velocity of light and fibre optic which is a function of the frequency of the light, or in the sonic domain the velocity of sound at standard pressure volume and temperature of the substance comprising the sound path to the host sensor junction 127.

Each half cylinder pair 173, 175, 178, 180, 183, 185, 188, 190, 193, 195, 198, and 200 rotate in opposing directions with phase synchronization at velocity and accelerations that directly correspond to the number and type of probing and echo samples for the active sensor band sequences of the current probe interval period. Such parameter may be varied by commands emanating from executives that originate from user interaction with cics 116, causing variations in the operation of the cybernetic jogging model 93.

Reference is expressly incorporated herein to Time-of-Flight Tomographic Signal Processing U.S. Pat. No. 4,075,883, for amplification of the meaning of the probe interval with respect to a specific partitioning of the physical spectrum, which in no way restricts the applicability of the method shown here as an extension to that method as being applicable to all sub-partitioned bands of the physical spectrum.

PROBE/INTERRUPT CHANNEL SELECTOR

Figure 14:
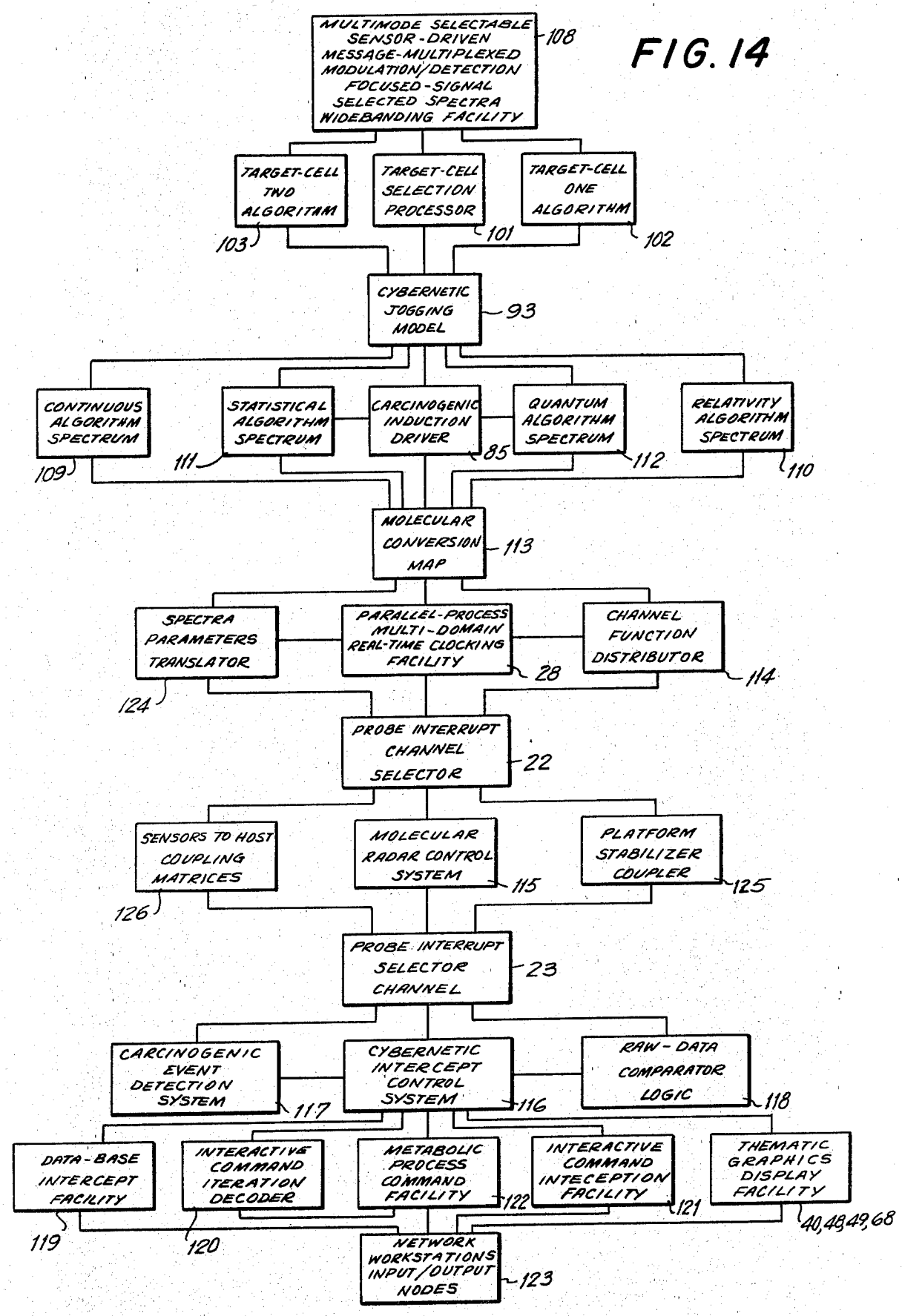
FIG. 14 is a function block diagram of the operating function of data acquisition.
Figure 15:
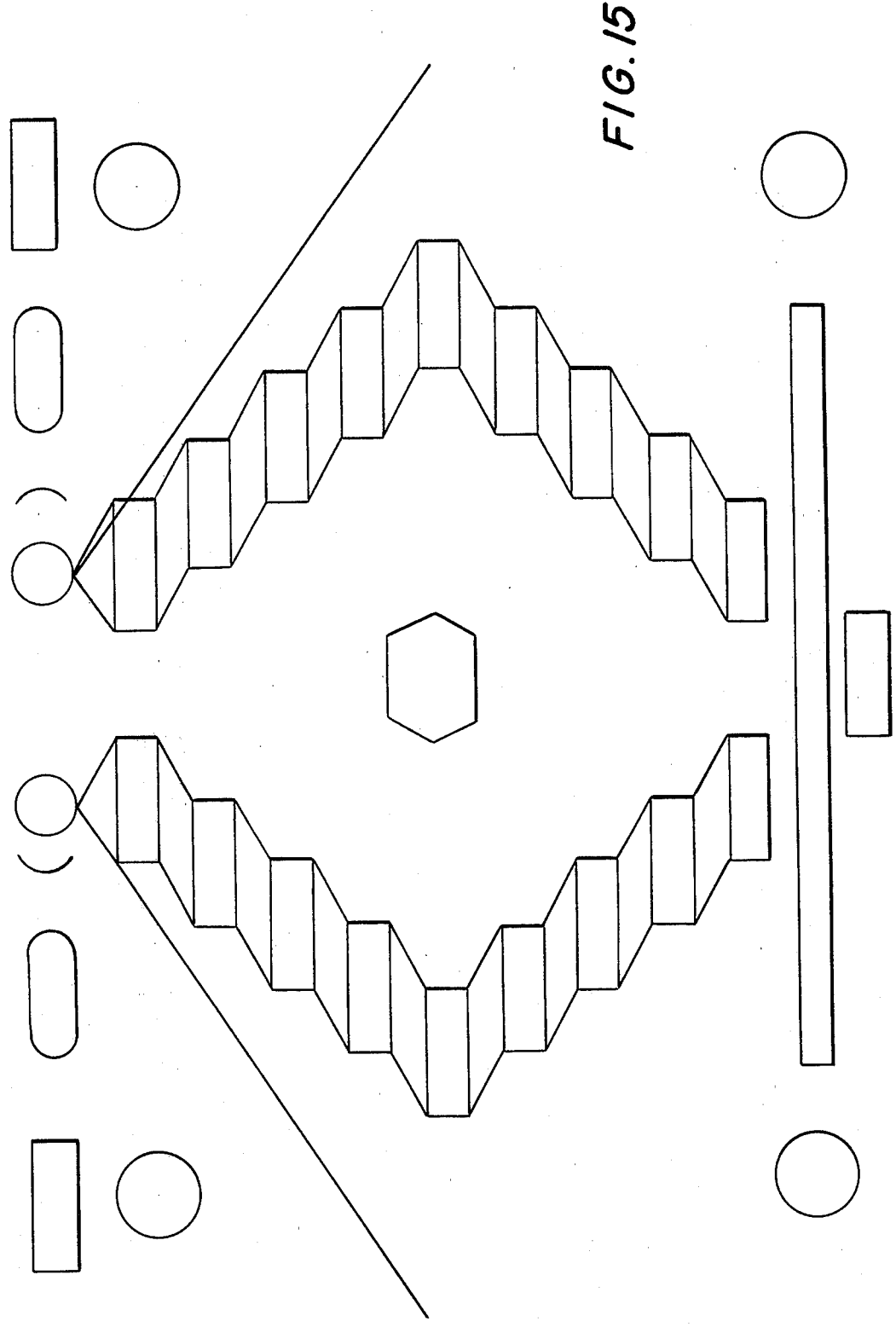
FIG. 15 is a function block diagram of a blank template for a user to configure their version of the experiment machine network system.

The pics is a controller-board with logic shown in FIG. 24 to support programmable vectored interrupts from a plurality of sensor-group-arrays. Having a sub-classified vectored interrupt hierarchy to support a further sub-classification of channels within a sensor-group, such means being the specified processing of a parameterized profile of the acquired data into a corresponding biological-record of segment thereof. Furthermore, the holes shown within the cross-sectional area of the ends of each cylinder in FIG. 14 are indicative of the channels that are information cavities traversing the extent of the containing cylinder to provide a path for signal propagation. To correspond to the sensor-group classification and channel sub-classification within each sensor-group there is specified a channelized signal-path, for each transducer selected. Each cylinder is, in the conceptualization to be considered as a wheel driven by a sensor motor at arbitrary velocities and acceleration in either the forward or opposing direction. Further, each of the cylinders can operate as described asynchronously or bisynchronously based on target-space requirements. Each cylinder embodies a form of a cycle containing holes used to form a multiplexing sequence of framing intervals of a device that is strobed periodically by passing a signal through the hole between a source originator and a destination detector. By positioning the holes in groups of ten and further subdividing each group, corresponding to the division of the physical spectrum into ten sub-bands of ten sensor-group-arrays, with sub-division within the sensor-group, different multiplexing patterns or partitions thereof are implemented. An algorithm that explains the operation of the four cylinders will be found in the following and is the means of the processed embodiment. Other algorithms may be envisioned as a consequence of the use of this invention, and hopefully result in additional improvements.

ALGORITHM FOR THE PROBE INTERRUPT CHANNEL SELECTOR. See FIG. 24

Figure 7:
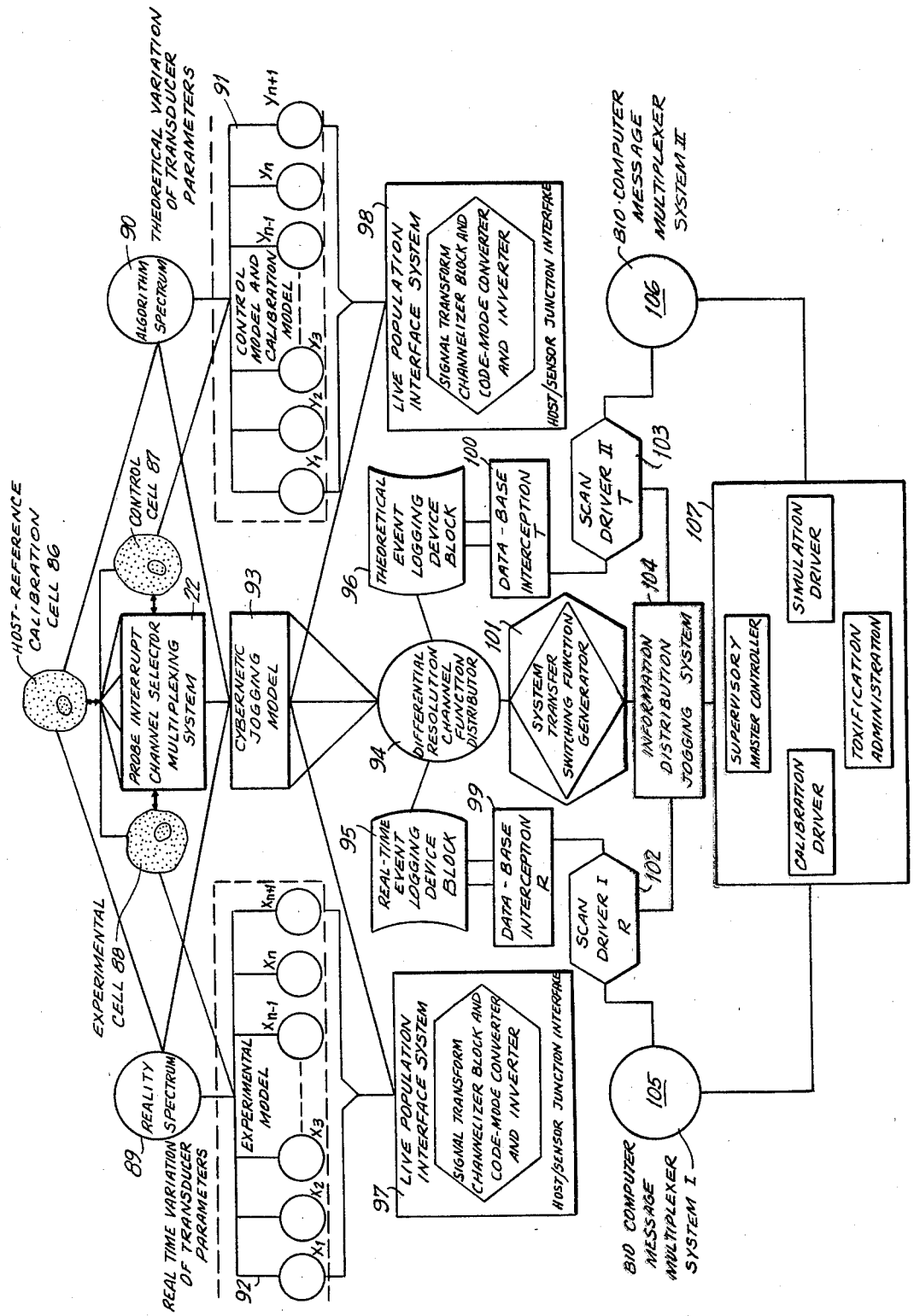
FIG. 7 is a function block diagram of classical experiment method relating to calibration, control, and experiment models.

1. Select time interval for probe frequency transmission burst through probe channel N defined by frequency and channel geometry and physical characteristics of channel medium, for each model, calibration control, and experimental as per FIGS. 21 and 22.
2. Calculate time span allowed and probe speed necessary to initiate burst frequency and trace to its first observable station, for Nth channel.
3. Calculate probe speed for spectrum burst receiver (on the transmit side), to frame target space for duration period (Ti) periodically, and to arrive at its first observable station to be digitized and stored. This is a means of spectral windowing.
4. Select the fundamental (base) probe frequency for the PICs being used, and load probe-wheel channel/frequency profile into storage to be used as a standard against which to quantify the observable burst spectra. Set transmission and reception intervals to coincide with strobing rate and channel/target-space intersection.
5. The observable burst spectra of channel one transmitter will enter the receiver cylinder while the spectra is digitized and stored. This event is always synchronized with a servo-type control system or an analog of such whose control parameters are continuously sampled and digitally processed to a data-base. Thus, all data retrieval and storage of such for any detectable event, is made available as a chronologically precise mathemaical sequence. The probe burst receiver channel is synchronized to the probe burst transmitter channel at optionally selected burst rates, allowing the observer to use different timing algorithms, and to observe physically as synchronizing patterns always describable in terms of frequency related parameters in the context of each of the four observation model specified as a means in FIG. 7.
6. PICS motors and oscillators are started and stabilized to the selected calibration state and verified.
7. Step six is monitored and its performance assured by the calibration stability block. As a component of the servo control system MORCOS the PICS I/O is synchronized and algorithmically restrained making all experimentally retrieved information available for use in devising new algorithms and designing new generations of multiplexing with a more powerful spectrum than the one before it, thus making this a recursive system having heuristic qualities of operation.
8. Start clock initialization procedure for currently selected probe channel interrupt interval (each sub-band of the transmission and reception channel paths has its own clock).
9. Read all clocks of step 8, and verify their coincidence with values selected in steps 1 to 5. If coincident, proceed to step 10, otherwise, repeat this step.
10. Upon obtaining a desired calibration pattern (the experiment is initiated here), at target/channel framing-interval coincidence, the first energy-burst probe spectra is fired at the target. As each channel becomes coincident with the target space previously selected, the characteristic frequency for that channel is filtered from the energy burst carrier spectra. The duration of the energy burst is defined by the physical properties and geometry of the transducers the velocity and accelerations of framing interval, and other varied considerations as per steps 1 through 9. Whatever options are selected, the corresponding band spectra-analysis are digitally performed in memory, stored and successively accumulated for a sample point transducer display on a spectra event per channel basis, for each of the physical models defined in the observers system. For each observation model, a separate subroutine exit is made to the DATA-BASE INTERCEPT module as follows:
   A. Time-band spectrum input (coincident framing interval).
   B. Energy-burst spectra input.
   C. Time-band half interval transmit spectra window.
   D. Energy-burst transmit spectra half interval output.
   E. Transmission probe spectra half interval band spread analysis-real-time.
   F. Receiver interval echo-spectra input (digitized coincident framing interval).
   G. Half interval receiver-echo-spectra band spread analysis.
   H. Whole interval receiver-echo-spectra band analysis.
   I. Translate each successive spectra by the MOLECULAR DATA CONVERSION MAP in preparation for data-base recording, FIG. 19.
   J. Adjust clocks for time taken by DATA-BASE INTERCEPT and exit subroutine.
11. Increment clocks by basic system time and subroutine exit to DBI, for administrative functions.
12. Has next coincident-framing interval begun? If not, repeat step 11. If yes, proceed to next step.
13. Read, digitize and store vidicon output spectra as per the previous steps.
14. Increments clocks by basic system time and initialize for next coincident framing-interval.
15. Compare the results of corresponding spectra of target/space output for the experimental target, calibration target, and the control target. Detectable differences are primed for display at these channels assigned monitoring stations as per the MOLECULAR/SPECTRA CONVERSION MAP, FIG. 13, and the data-base assignments, FIGS. 16 through 24. Repeat algorithm from step 8.

Where the mechanical embodiment of the PICS is shown in FIG. 5 to form a useful analog for reference and understanding, the preferred embodiment requires that the PICS be fabricated as a printed circuit board using the most advanced grand-scale of integration available, to enable the inclusion of the new sensors, compatibly designed. Further to have on-board firmware and high speed random access memory that will recognize user supplied sensor operation-band scaling parameters that will enable the inclusion of newly designed sensors without other changes necessary. As stated in previous paragraphs, the molecular identification spectrum of a biological-computer is limited only by the operating band of the sensors used to, populate the sensor group arrays. Such hardware is offered in numerous configurations by many vendors.

The PICS is the facility that allows a user to configure the operating band-width of each individual member biological-computer in a cluster of biological computers separately in accordance with the needs of the experimental context of interest and by operating under the centralized control of the experiment machine's information distribution protocol, which tailors the operating spectrum of the overall experiment-machine bandwidth to those pluralities of biological-computers, becomes a means for evolving a limitless number of biological computers, each having its own unique bandwidth in its operating spectrum simply by populating the sensor-group-array interface with a unique configuration of transducers. With the PICS as described or some embodiment thereof, this is now possible.

REAL-TIME BIOLOGICAL-MESSAGE INTERCEPTION INFORMATION RETRIEVAL NETWORK

As biological records are stored somewhere in a supporting data-base, the information organization of the distribution network itself is a simulated representation of the target space(s) to which the biological-computers are attached; taken collectively, the biological information network distribution profile of any given instant is a biological-record itself representing a real-time model of the associated probed target spaces. For example, if a section of a pituitary gland were to be the target of the host/sensor junction, and the required sensors were so attached with the required pluralities of clusters of associated biological computer, when put in operation the extracted biological records will be distributed from a record interception data-base in accordance with a protocol in which EXM work-stations would be designed to receive selected characterizing biological records. By providing a sufficient number of so designed workstations and distributing their biological records as they occur, an eagle-eye view (a global profile) of the information distribution network is a sensory driven real-time model of the section of the pituitary gland targeted. From this perspective, the pituitary gland becomes the back-end processor to the front-end Experiment-Machine, with biological-computers as the simulated components of the pituitary gland harnessed by sensors. The facility to intercept each biological record and dispatch it to the RIBMIIRN without going through the data-base hierarchy, where it's stored, keeps the ongoing operation of the Experiment-Machine in a concurrent real-time mode. To view the distribution profile, the cybernetic intercept control system—FIGS. 20, 21, 22—designated in the primary embodiment as the umbrella facility available to the Experiment-Machine user, enables a distribution profile snapshot to be displayed as a sequence of iterated symbols in a working model (real-time and dynamic) of the cluster sensored to the biological computer. By coordinating the operation of this facility with that of and in conjunction with biological radar, molecular identification data-base, the probe interrupt channel selector and the overall operation of clusters of biological computers in an Experiment-Machine network system, are implemented.

Figure 6:
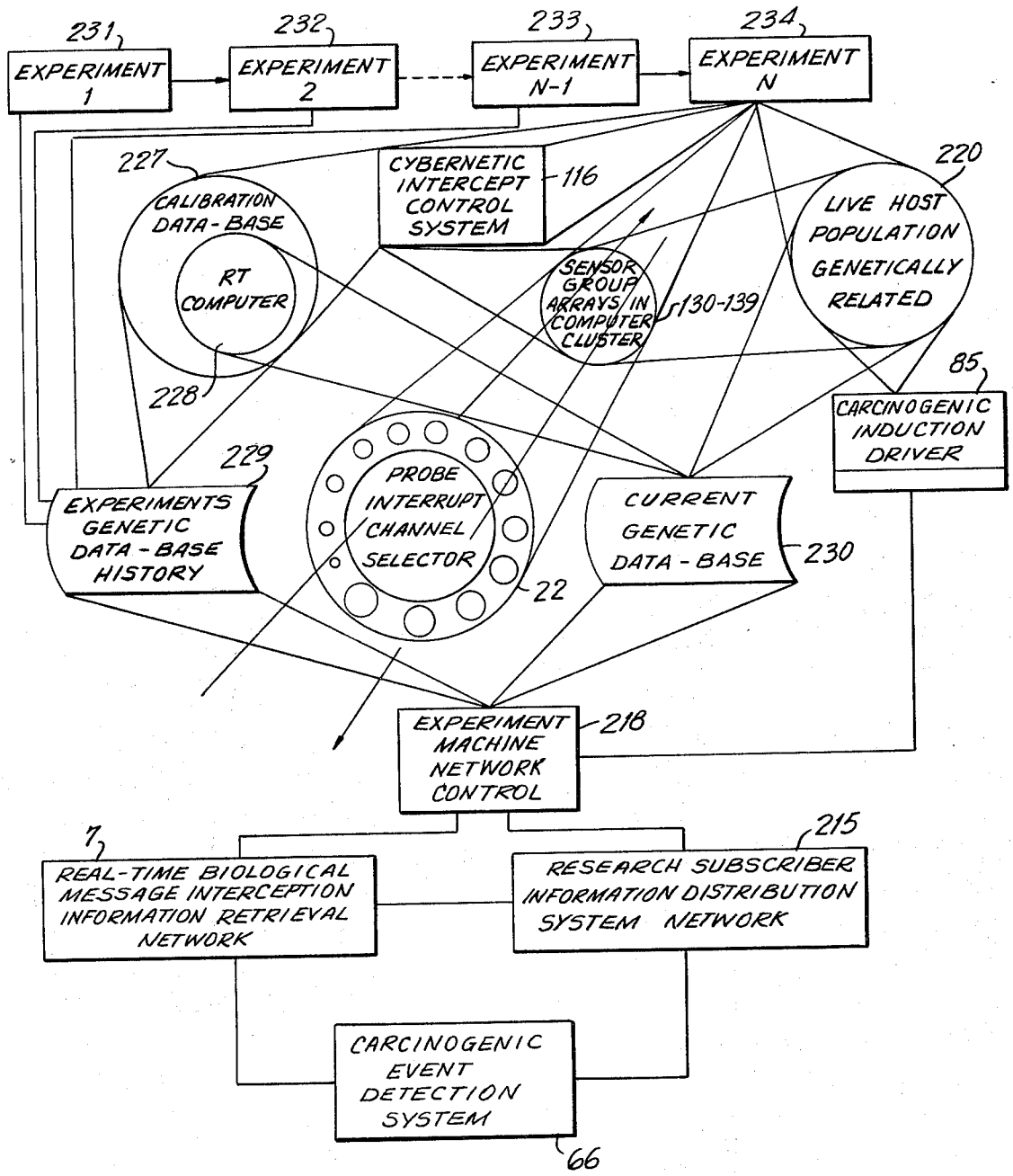
FIG. 6 is a function block diagram of tracking of genetic history data base.

Referring now to FIG. 6 overall conceptual design relationships amongst the major modular constructs of the experiment machine network system are shown. Starting with the live host population genetically related, 220, which correspond to 235 through 243 in FIG. 2 and connected to sensor group arrays in computer clusters 130 through 139. Under the control of the cybernetic intercept control system 116, also FIGS. 16 through 24 being flow charts describing the sequential operating procedures of 116, the probe interrupt channel selector 22, flow chart FIG. 24 operates the coordinated and synchronized data-acquisition algorithm which populate the current genetic data base 230 with data from current probe-intervals. All such current acquisitions are archived to the experiment's genetic data-base history 229 which is specific for host population 220. The calibration data base 227, managed and directly controlled by real-time computer 228, provides simultaneous real-time access of 229 and 230 to the controller of the current in-flight experiment, the experiment machine network control system 218 so that a recognition trend may be detected when current data-acquisition images are seen to compare with images stored in 229 that have been documented as symptomatic of a carcinogenic process or other divergent or anamalous metabolic condition. As there are hundreds of billions of cells even trillions of cells in higher primates, and in humans something of the order of 70,000 different cell types, the quantities of data that can be acquired practicing this method requires a network of observers to maintain this acquisition at a real-time level.

This research subscriber information distribution system network 215 is positioned to be in three way bidirectional communication with the real-time data-acquisition process through services provided by 218. In exchange for these services, 215 is charged with the responsibility of being on-line while the experiment is in flight and reporting promptly through a data input-means any observation made of events in a class for which it has subscribed to be a receiver of. The timely execution of these functions, distributed in clusters of subsidiary networks broken down into a hierarchical protocol directly related to the functional physiological and metabolic hierarchical protocol of 220 allows the incorporation of such reports as 230, and subsequently 229. The real-time biological message interception information retrieval network 7, is at the service of 218 and is of sufficient size to support the current quantum levels of data-acquisition and the membership size of 215. As the information acquisition density appearing in 7 and 215 approaches the real-time information exchange densities that actually take place in the metabolic domain of 220, the number of observer workstations must increase accordingly to provide for the time incorporation of observed events into 230 and 229; else 218 ceases to be a real time system. Assuming reasonably sufficient resources, with a network of trained medical observers, it is now possible to introduce a carcinogenic induction driver 85 to live host subject 220 at the level of nuclear molecular structure, capture and store the immediate and prolonged consequence of such introduction in 229, and subsequently use such information to refine the significance of 230 as it is viewed at 215 to the extent that the first event (that is the intra cellular kinetic metabolic event, or the collection of the same if there is more than one such that inter cellular kinetic events, are required at minimum) that is carcinogenic becomes a known parameter of the species involved as represented by 220.

The carcinogenic event detection system 66, consists then of all that is shown in FIG. 6. The experiments shown in 231, 232, 233 and 234 are in fact the successive metabolic replication sequences that take place within the life span of 220 as well as to the perpetuation of 220 to its progeny, to the extent that eventful carcinogenic tendencies in current host subjects are transmittable to their heirs.

This invention shows that the caption at the top of FIG. 10 "Family of Experiments." Forecasting Properties of The Current Generation G(n) is greater than the forecasting properties of the previous generation G(n−1) is in fact true.

MOLECULAR IDENTIFICATION CONTROL SYSTEM. See FIG. 16 through FIG. 24

The molecular constitution of chemicals in general and of organic chemicals in particular becomes known through the measurement of physical indicators such as temperature, emission/absorption spectra, density, color, and pluralities of other physical conditions. One example would be the color response of litmus paper, when exposed to a fluid depending on whether the fluid was alkaline, neutral or acid, in correlation with thermal properties.

The experiment machine has access to ten sub-classifications of sensor group arrays. Each sensor-group sub-classification by itself prescribes the operation over a characteristic bandwidth partition of the physical spectrum of an associated sub-classification of a family of transducers which are used as indicators of specific physical events and special chemical reactions or states, both steady and transient. Within each sub-band effective analytical resolution of the physical and chemical events over a time-span are recorded while interactively responding to gradients within that bandwidth by providing feedback. The physical indicators also known as transducers are correspondingly sub-classified into ten families of detection and ranging transducers that are meaningfully operable within the respectively associated sub-bandwidth of the physical spectrum as they are selected. Each one of the ten partitions is correspondingly further sub-divided into ten sub-bands of the transducer-family. Defining that bandwidth, there is a unique channel for each transducer to operate within a selected portion of the associated bandwidth and the ten transducer-partitions, overlapping their operating range into the operating range of their adjacent neighbors resulting in a smooth, continuous operation spectra of the bandwidth as if there were only one transducer having an operating bandwidth in the spectra of the defining collection of sensor-groups. This means provides for the ability to integrate new generations of sensors as they become available without changing any firmware, hardware or controlling software.

The iterated states of a cluster of sensor groups' characteristic spectra is a means of tracking said chemical states in the physical context indicated by the operating states of the relevant correlated sub-classes of transducers.

A specific embodiment of combining the operation of one member from each of two or more specified sensor groups, that of acoustic and optical band is described in U.S. Pat. No. 4,011,748—Method and Apparatus for Acoustic and Optical Scanning of Object—demonstrates the advanced analytical progression when combining the operation of two or more sub-classes of transducers. The primary embodiment of this invention specifies that any permutation and/or combination of transducers may be combined in either parallel or sequential over-time operating modes to place the associated biological-computer in a status indicative of the chemical composition and physical context that the correlated sensors are responding to.

Figure 4:
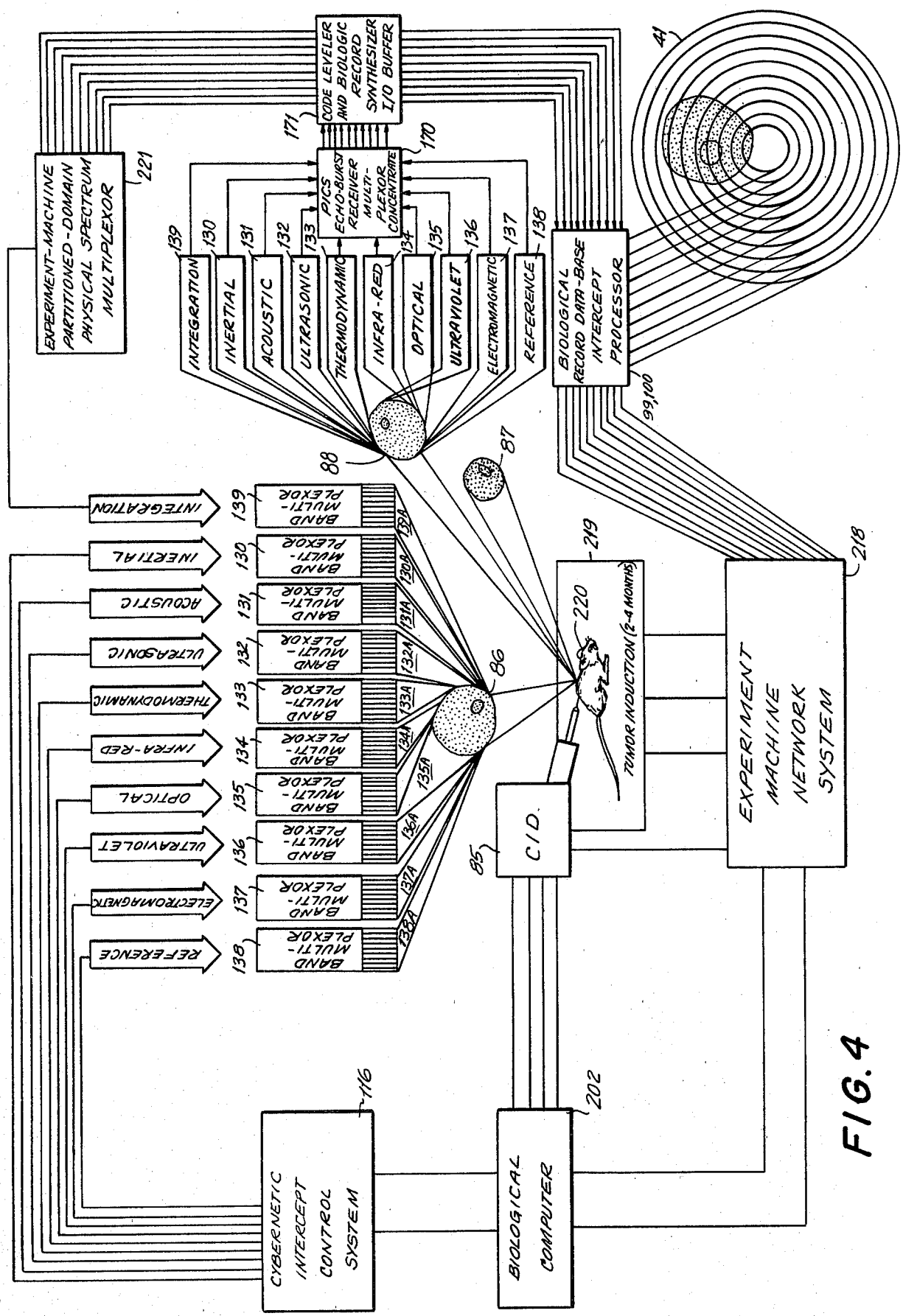
FIG. 4 is a function block diagram of interfacing between related control systems.

Referring now to FIG. 4, the scientific method is shown as embodied in the living biological environment in which biological computers operate cells 86, 87 and 88, are situated at the top of FIG. 4, as they are the original precipitators of all information that finds its way into the experiment machine information access paths. Probe interrupt channel selector multiplexing system 22 controls the scanning algorithms, selecting from the algorithm spectrum 90, the corresponding formulae into operating memory to programmatically perform the calculations that conform to live data retrieval from the reality spectrum 89. 91 shows the numerous membership of algorithms noted as y(n) called theoretical variation of transducer parameters, and called the control model and the calibration model, as the algorithm spectrum is used in behalf of both these cell types. The experimental model 92 consists of all of the transducers used to communicate the acquisition of data and in this invention they are classified in accordance with the partitioning of the physical spectrum 130 through 139-band 1 through band 10. In any probe interval operation of pics a combination of transducer types are selected so as to be able to produce output signal spectra with signature bearing characteristics of the molecular structure of the segment of the cell being scanned in the current probe interval. Flow chart in FIG. 24 characterizes the specific operating logic of the probe interrupt channel selector. The cybernetic jogging model 93 coordinates this signal processing for the three cell types by modulating and demodulating the results of algorithm selection computation from the algorithm spectrum of the control and calibration models 91 and 91a with the real time data acquired from the reality spectrum 89. In the course of operation of 22, the three cells 86, 87 and 88 may and in the hands of skilled users will in fact exchange roles with each other in turn, in order to achieve the calibration state of the experiment machine network system. The cybernetic jogging model 93 is the sum total of all the states, networks, sensors, cpus, and memories, taken collectively in any instant of time to coordinate the retrieval of biological records based on comparisons of corresponding scanning patterns of cells 86, 87 and 88. As relative motions are detected at host sensor junction 127, by information received from differential resolution channel function distributor 94, the cybernetic jogging model 93 acts to separate the portion of motion that was caused by physical momentum and the portion of motion that was caused by cell kinetic processes, both motions collectively forming the relative motion detected at host sensor junction 127 thus permitting the automatic generation of signals required to re-aim the currently active sensor groups the original target position before the relative motion was detected at HSJ 127. This feature is called biological radar 129, in FIG. 13. Real-time event-logging device block 95 represents storage of reality spectrum information 89 and theoretical event logging device block 96, represents storage of algorithm spectrum information.

Data base interceptors, for the reality spectrum 99 and algorithm spectrum 100, facilitate the bouncing effect between the probe interrupt channel selector 22 and the cybernetic intercept control system 116. The data base interceptors 99 and 100 coordinate the separation of relative motion into their physical motion component and metabolic process component by providing the tracking of a selected target, either 86, 87 or 88 concurrently, or all three, or two of three, simultaneously in sequential combinations, up to and including all possible combinations.

Scan driver I(r) 102 and scan driver II(t) 103 coordinate the orderly exchange of information for the reality spectrum 89 and algorithm spectrum 90 with the biocomputer message multiplexer system I, 105 and biocomputer message multiplexer system II, 106 with 95 and 96. Using input from the scan drivers 102 and 103, 105 and 106 format the information received for the controller-driver and administrator 107. The host/sensor junction interfaces of the experiment subject(s), 97 and 98 for the reality and algorithm spectrums, synchronize the mode of signal transmittance with the mode of reception expected by the multiplexing system 105 and 106, as these expectations are modulated by 102 and 103. The controller, drivers and administrator of 107 communicates with information distribution jogging system 104 and with each other, to cause 102 and 103 to restrict or enhance the passage of certain types of information exchanges depending on the dynamic requirements in a probe interval to aim sensor(s) or restore and maintain a calibration state.

Information distribution jogging system 104 interprets information received from system transfer switching function generator 101 in the format that it expects as to how the information generated in the current probe interval is influencing the calibration state of the entire system with respect to the scanning of 86, 87 and 88.

BIOLOGICAL-RADAR

The means of target tracking, collision avoidance, intersecting trajectories, and navigating in the blind have been in the province of marine, airborne and submarine navigational systems. As known to those versedin-the-art, modern radars can pinpoint distant positions, arrange for the coincidence of moving objects of known position, identify and characterize geometric topology of a distant moving target that happens to appear on a radar screen, or aid the return of planes to a mother-skin.

The means to navigate the sensors of a biological-computer to a selected position and lock the sensors to that position is enabled in this embodiment by the facility described as biological radar. Operating in conjunction with the sensor manipulation facility, the EXM platform stabilization system, the Probe Interrupt Channel Selector, and the Molecular Identification Data-Base, the Real-Time Sweep-Pattern Display Terminal of the EXM workstation—FIGS. 3 and 11—fashioned after the conventional Radar Display Set known to those versed-in-the-art, is the EXM workstation display that is specified to facilitate Biological-Radar. Whereas the echo-range of prior known radars pertain to the geo, astro, and oceanic topologies for sub-marine, surface, airborne and spatial navigational requirements, the echo ranging capability embodied in experiment-machine Biological-Radar facility is responsive to position changes at the order of microns and angstroms to conform to the molecular topology of cell definition, is the means to reflect the topology of the sensor/host junction.

Figure 18:
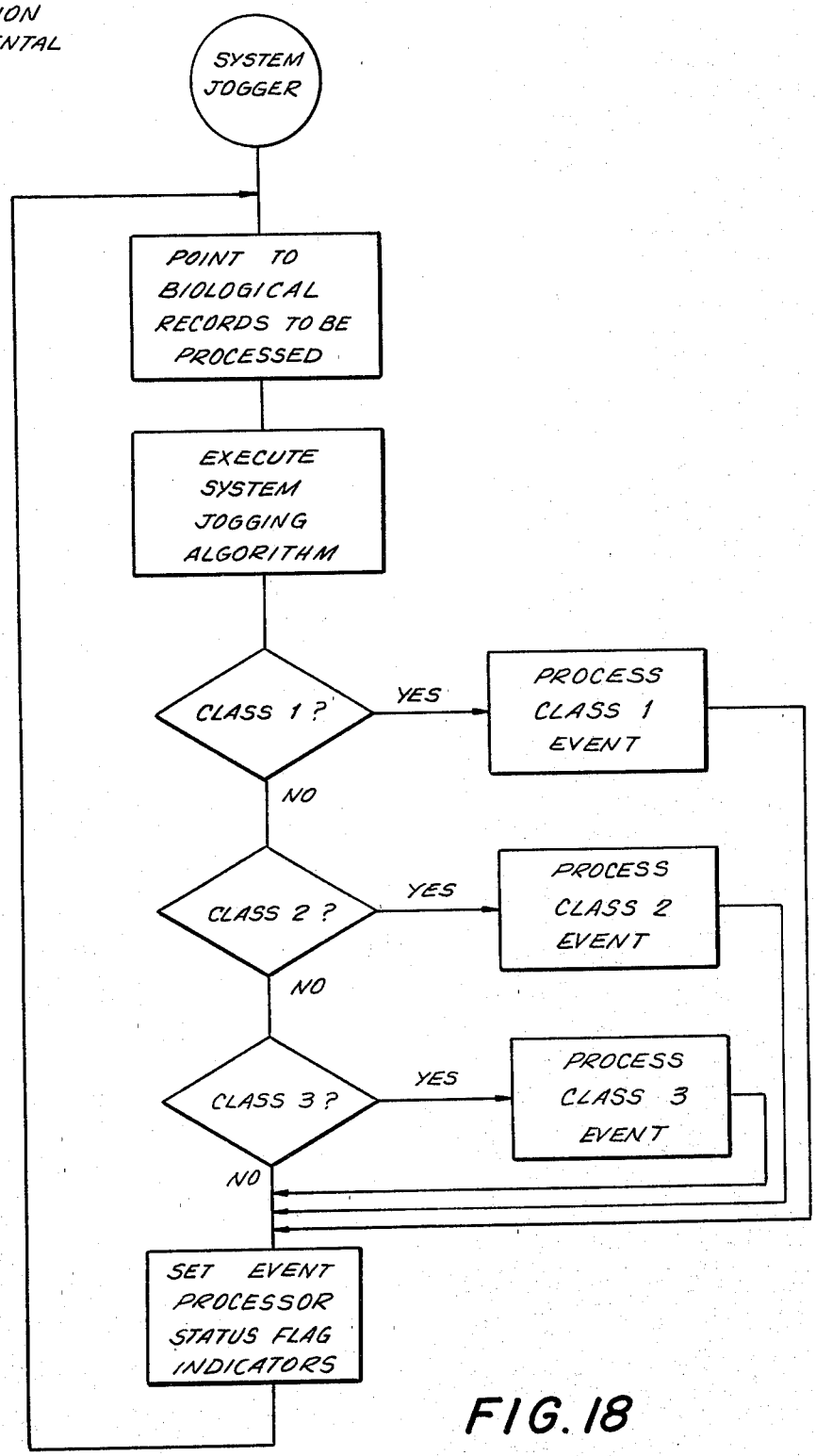
FIG. 18 is a flow chart of the experiment machine event classification system jogger.
Figure 22:
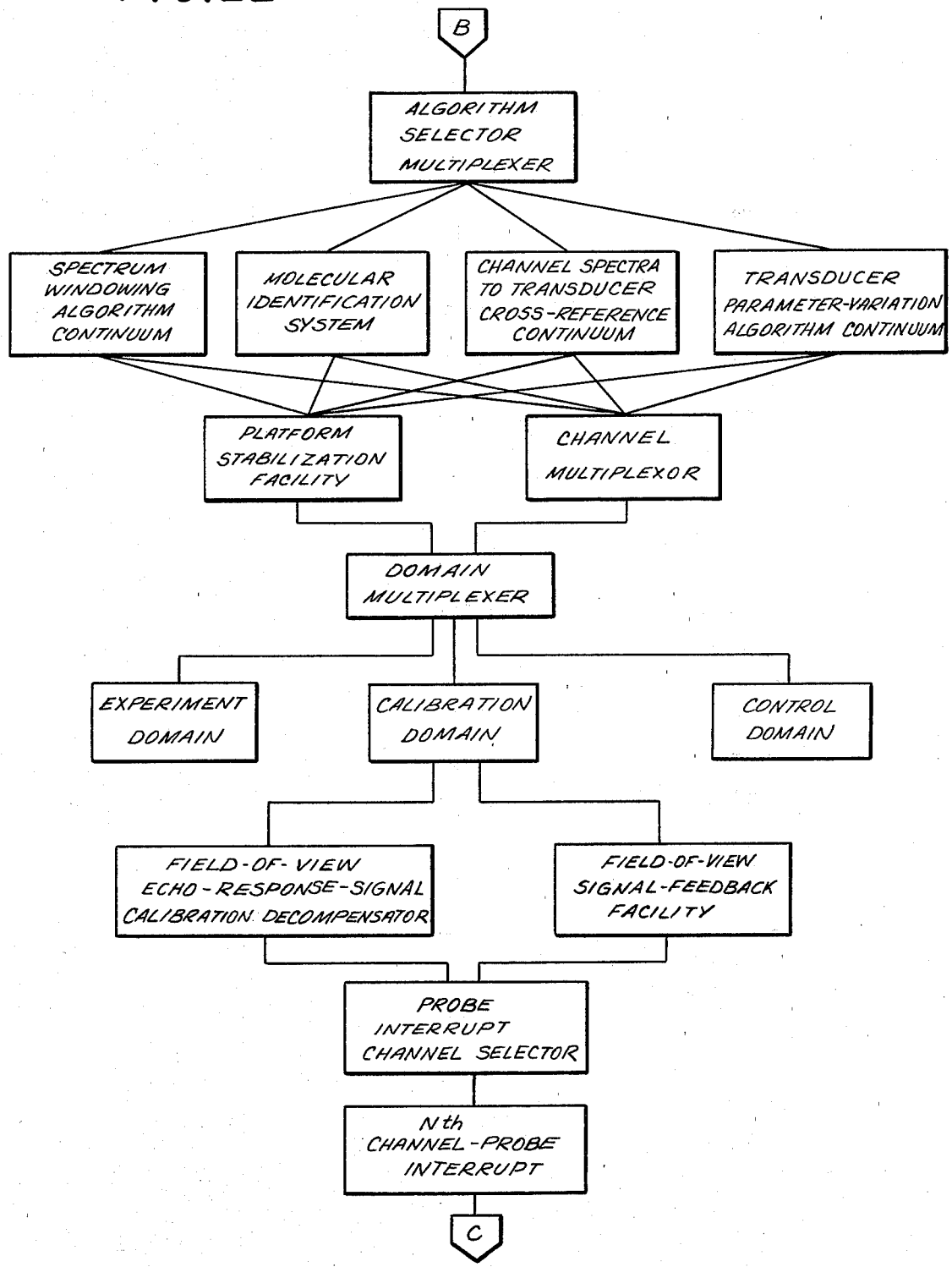
FIG. 22 is a flow chart which is a continuation of FIG. 21.
Figure 23:
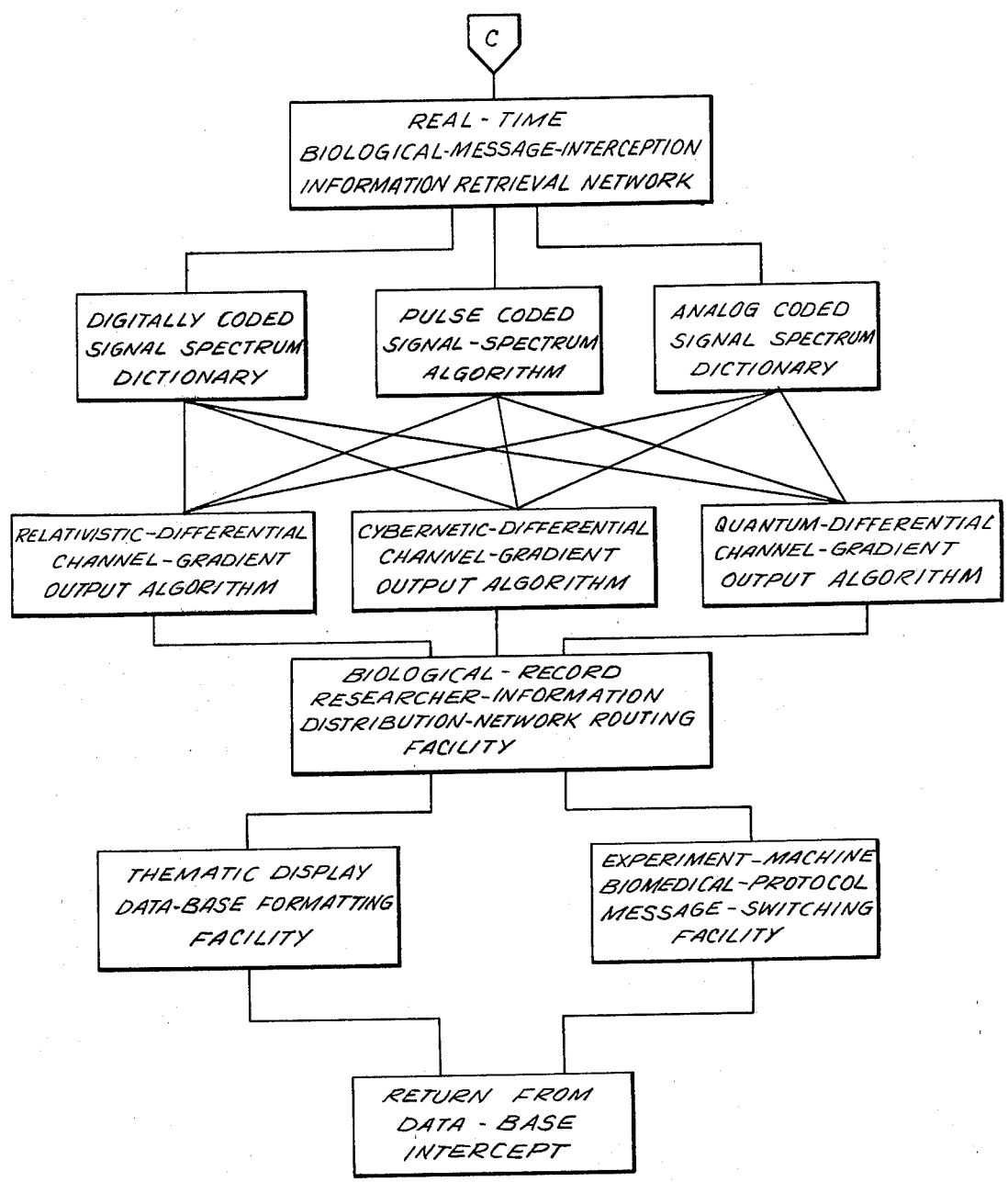
FIG. 23 is a flow chart which is a continuation of FIG. 22.

The concentric areas shown in FIG. 18 labeled in accordance with the sub-classification of the physical-spectrum already described, represents the operating band of the sensor-group associated with it. The width of each of the concentric areas represents the temporal scanning interval of the sensor-group as previously described. As is shown in FIG. 22 and FIG. 23, cells of different type, size and metabolic state will be multivariationally and interactively responsive with respect to the operating spectral scan-band of the relevant sensor group, with ten different hues of indication, to correspond to the ten sub-divisions within a sensor-group partition, as defined, as well as concurrent operating states of the other sensor-groups (including respective sub-classifications within the sensor-group). As relative motions described occur, a report of the exact nature of the relative-motion with respect to the operating components of the biological-computer cluster, the sensor/host junction(s) and the selected field-of-view is reported to a data base. The detail of specified interpretive protocol, characteristic of a particular requirement is not in the scope of the primary embodiment described herein. Although symbolic organic-chemistry's nomenclature may be preferred by one group of participating researchers, a pure color representation as shown in FIG. 18C may be specified by another participating group, and still another participating group may prefer protocol entirely their own, such as sequences of colors, symbols of some combination of both in some meaningful yet arbitrary format, since the meaning is, in fact, a matter of interpretation. Others may prefer a quantified graphic representation by which basic developmental themes may be extracted and displayed on a real-time interactively operating basis, in terms of quantified parameter.

The mapping of the Biological-Radar Display conforms to the topology of the sensor/host junction. The view shown, as is known to those versed-in-the-art, is a cross-section, or a projection of such, of concentric conic sections, corresponding to the micro geometry of the probe wands at the host/sensor junction.

As different partitions of the sensor/host junction become operable in conjunction with the operation of the Probe Interrupt Channel Selector, the focus of field-of-view of the selected target space will shift, notwithstanding the shifting caused by selective motions intended for exploration.

This shifting of the field-of-view will be observed on the Biological-Radar Display Set. A single target cell, provided the co-requisite sensor-group bandwidth sensitivities are met, can be isolated in the field-of-view and parts of it specified for further probing and experimentation, by selecting the appropriate range scanning scale.

Figure 8:
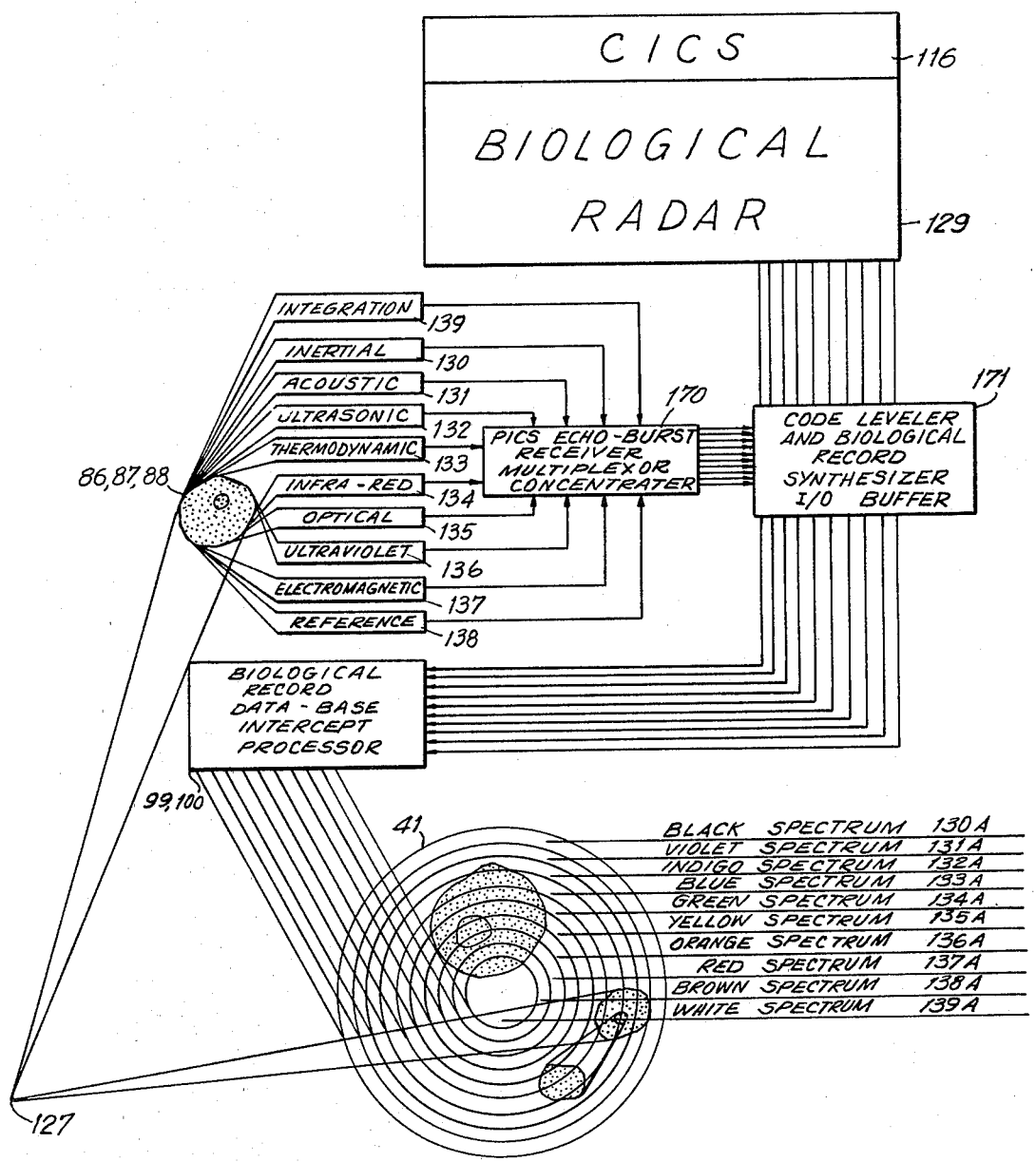
FIG. 8 is a function block diagram of biological radar annunciation monitor located at network workstations.

Referring now to FIG. 8, the translation of a probing sequence of the current real-time probing interval, into images of two cells and a third image of the nucleus of all of the cells is shown being visually formed on the biological radar workstation annunciator monitor 41. Each concentric band of 41 corresponds to a partitioned domain of the physical spectrum 130 through 139 and subdivided narrow band channels 130A through 139A, and is so tagged by a characteristic color as marked on the drawing. The sweep pattern in each concentric band will be synchronized with the probing sequences of the current interval with respect to the cross sectional geometry of the HSJ 127 and the relative position of the selected target cell with respect to that cross sectional geometry. As typifying color sequences are repeated that uniquely signify the amino protein molecular composition of the so selected target space, the concentric band sweep pattern at the position on the screen that corresponds to its position in the host sensor junction 127 will be interrupted for a duration at the sweep pattern velocity that will cause the image formed to be in exact proportion to the size of the molecule in the field of view that caused the sweep pattern interruption. A combination of colors in coordinated synchronization likewise reflect the sub structural composition of target spaces, the scaling of the concentric display can be expanded and contracted to correspond to activations of larger and smaller proportions of the active sensor groups in the field of view of host sensor junction 127. Sweep pattern velocities can likewise be modulated.

Pluralities of clusters of such display stations may be simultaneously on line to support many pluralities of such real time imaging of a variety of cell types produced simultaneously by pluralities of biological computer clusters so that the selection of colors can be arbitrarily made to correspond to the cell physiological protocol that is the natural characteristic of the amino protein sequence that governs a certain cell type, or substructure thereof.

Furthermore, where it is found that the probing energy is not in the optical band per se, that typically signifies the comprising molecular identification, the concentric color sweep pattern assignment may be made to correspond with respect to each narrow band sub division of the typifying sub domain of the physical spectrum. If all 10 bands of the physical spectrum were active in a probe interval, then 10 such displays, each having a color sweep pattern definition unique to its associated transducer type operational spectrum would be required. Furthermore, to demonstrate the power if we discard the cardinality of visibility, it works equally well if the other physical subdomains were sufficient to uniquely identify the comprising molecules of a targeted tissue space without the optical band. Thus uniquely characteristic sound sequences can be associated not only for varieties of cell types, but also for the structural sub components whose differences cause cells to be of different types. Reference is made to the February 1980 issue of Omni Magazine for an article entitled "Listening To Life" describing work, which demonstrates this capability.

Other types of transducers may also be so adapted for modulated sequential annunciation where it is seen to be effective and economic within the scope of this invention. It is intended to claim privilege of exclusive right for practicing this method to the extent entitled with respect to the entire physical spectrum, and all known associated transducers.

CARCINOGENIC EVENT DETECTION SYSTEM

Figure 13:
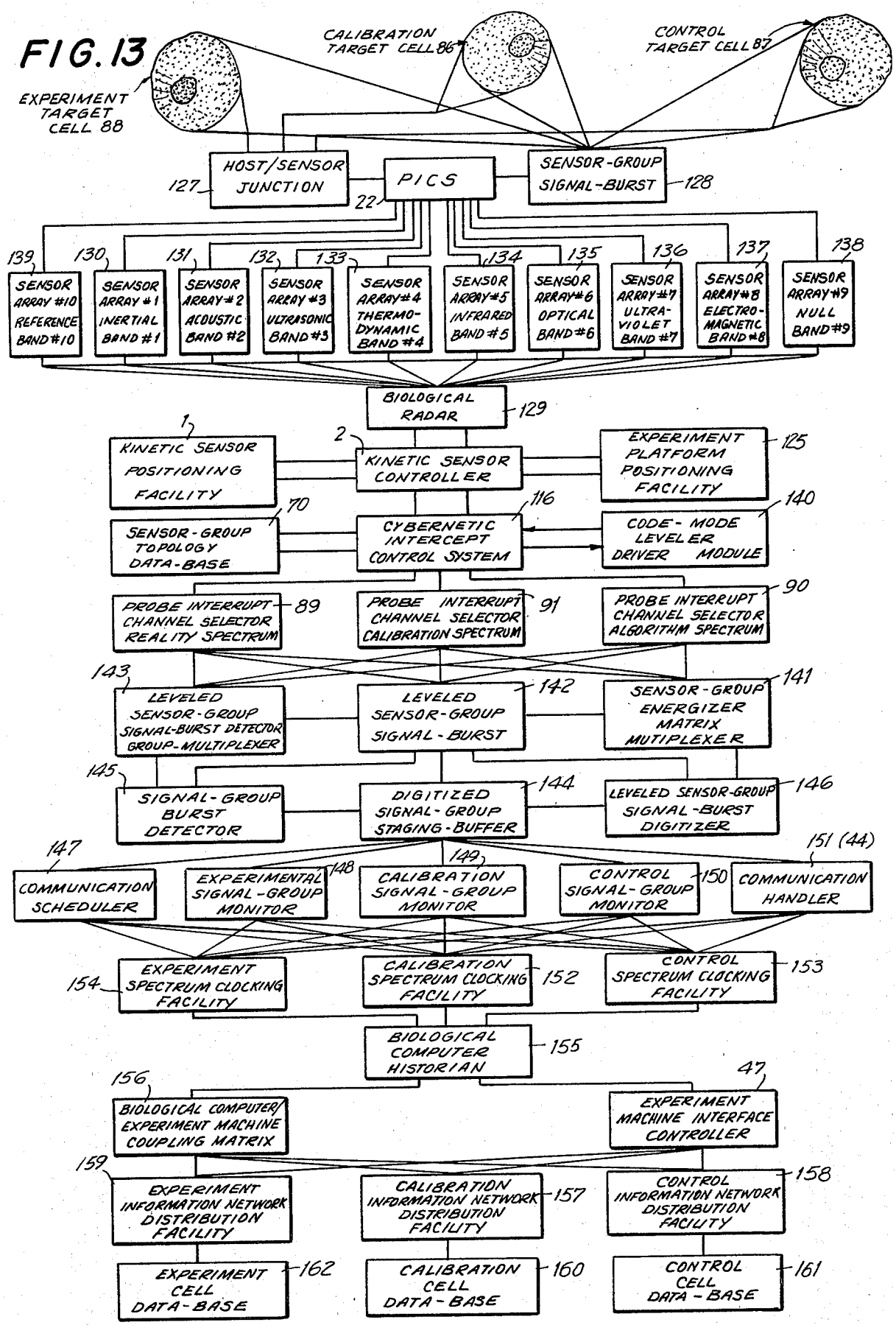
FIG. 13 is a function block diagram of the operating function of data acquisition and network processing.

When the procedure described in this section is followed, the Experiment-Machine system becomes the Carcinogenic Event Detection System—CEDS. Using selected guinea pigs or the like, a configuration of clustered biological computers specifically adapted to the desired application is placed in an operating state as follows:

A minimum of three positions on or in a guinea pig are connected to a biological computer via the user specified sensors the cell(s) type(s) in the three fields-of-view of the three connected positions must be of identical type(s) and in the same metabolic phase state with respect to each other. The Kinetic Sensor Manipulation Facility, indicated in FIGS. 13 and 3 is used to direct the positioning of the sensor/host junctions of the three respective biological computers so that the conditions of field-of-view equality will exist. When this condition is achieved using the sensor guidance logic algorithm shown in FIG. 17, the biological records emanating from the three different positions will be equivalent. Incorporate by reference for sensor manipulation U.S. Pat. No. 4,084,209.

There are no logical restrictions aside from the constitution of the guinea pig to adding more biological computers with adjunctive functions to this procedure, such as sensor refinement, or enhancement and amplification of more elaborate combinations of organic functions within the hosting guinea pig. A minimum of three is needed to implement CEDS in accordance with the scientific method. One field-of-view is called the experiment population, the second field-of-view is called the control population, and the third field-of-view is called the calibration population. When properly initialized, the calibration field-of-view will cause the source of the driving signals to be input to platform stabilization and biological radar facilities, while the other two fields-of-view will be maintained in sequence-following-state to the calibration field-of-view. When the desired calibration state is achieved for this experiment, the Experiment-Machine is, on command, placed in a lock-on-target-state by the Toxification Administration Facility shown in FIGS. 2, 7, 14, 15, 3, 12, and 4. The Carcinogenic Induction Driver has automatic control over the plunger or trigger of the device used to inject or otherwise administer the desired carcinogen. An example of one type of device is the Hamilton ML-P (microlab-p) designed as a hand pipette modified with suitable interfacing to allow its management by the Carcinogenic Induction Driver. To prepare for the initialization of the carcinogenic experiment, the carcinogen-bearing instrument is aimed at the field-of-view of the experiment population. On command, the device is triggered and the carcinogen is applied to the cells specified in the experiment population field-of-view. As the effect of the carcinogen ripples into the metabolic infra-structure of the host guinea pig, the biological records emanating from field-of-view of the experiment population receiving the carcinogen will vary to whatever deviations are caused by the attacking carcinogenic agent. The deviations are extracted as a critical-sequence (see FIG. 3), processed into the Experiment-Machine data-base, and saved for future use. In accordance with the description of this current experiment as it was described by Lloyd J. Old (Scientific American, "Cancer Immunology" May 1977) the connections of the cluster of biological computer must be maintained until the desired carcinogenic effect such as a tumor is observed. Consistent with the classical experiment, the subject guinea pig, having been selected from a specially inbred strain of guinea pigs, having been known to possess certain selectively bred immune response characteristics, undergoes surgical removal of the tumor.

The second phase of the experiment requires implantation of cancer cells from the removed tumor to the originally subjected guinea pig, as well as to a second guinea pig not having been selectively bred at all, but being of the same species as the first one. The difference between the experiment as described by Dr. Old and the experiment as performed in the primary embodiment of this invention is that the second phase is performed in precisely the same fashion as the first phase using clusters of biological computers in an Experiment-Machine system. The biological records emanating from the respective experiment control and calibration-field-of-view, and the attendant differences between the corresponding biological records are available, as in the first phase, on a concurrent real-time basis. In accordance with the results of this experiment, as reported in Dr. Old's article, the biological-records attendant with the introduction of the tumor cells to the experiment field-of-view will bear the indications of immunological resistance specific to the type of tumor cells administered while the biological records of the experiment field-of-view of the second host guinea pig, the one without the selectively bred immune response characteristics will bear the indicators of the failure of that host guinea pig's immune response system to successfully resist the carcinogenic attack. Real-time variations of this experiment may be performed within the scope of this invention, using pluralities of guinea pigs having a variety of genetic characteristics, mixing both related and unrelated members of the species to generate pluralities of generations of biological records for real-time comparative analysis, yielding precise descriptions of the biological-records that are attendant with the physiological syndrome being experimented with. For example, in the embodiment of the experiment as it has been described, an additional connection to glands associated with the vital metabolic functions of the host guinea pig, such as enzyme-initiating hormones, releasing glands are connected to biological computers via sensor clusters so that their attendant biological records may also be extracted, then a permanent computerized record of the progressive infiltration of the carcinogenic attack on the host guinea pig's matabolism will result, allowing the use of this data in the performance of future experiments on future relatives of the continued generations of experimental animals.

The genetic relationship to the inherited family characteristics relating to vital metabolic functions is precisely identified in the generations of biological records born from using the Experiment-Machine system on successive generations of members of a specific family with respect to a particular syndrome, or as described in this primary embodiment, a particular carcinogen. Critical sequences identified from previously extracted biological records isolated by this iterative procedure become available for comparison to current real-time biological records so that a trend can be ascertained in a current application of the Experiment-Machine system whereby a current biological record may be seen real-time becoming a record bearing the signature of the current target-cell.

Thus, early warnings of the incipient progression of a biological-record may be formulated into an early warning critical sequence biological record. After successive applications of experimentation as described herein to several generations of a specific family of experimental animals, a genetic data-base will exist for members of that family. Subsequent experiments on members of that family will have access to all of the critical sequences previously extracted. To the extent that such information is relevant, a prediction spectrum of the Experiment-Machine system will be enhanced each time new critical sequences are added to the database. Then, with respect to a particular family within a species, the Experiment-Machine system evolves into a forecasting machine having properties specific to the host subject(s) and its respective network of data bases.

Referring now to FIG. 9, the concentric ring biological-radar display, 41, that maps the subdivisions of the chosen partition into all the visible colors plus black, which is the absence of all colors, white, which is the presence of all colors, and brown which is a derived color into the remaining physical partitions of the complete spectrum. Recalling that 41 is a scaled representation of the host-sensor-junction, also being included in the target space, field-of-view, 9 shows a segment of a target-cell being displayed in band 3, being in this representation the ultraviolet band. If in fact ultraviolet radiation was used as the probe energy used to elicit the echo response at the position shown, and indigo was selected to be the color representing the ultraviolet partition of the physical spectrum, then all such targeted tissue space comprised of molecules uniquely identified by such probings with ultraviolet radiation will appear in band three which in this drawing is colored indigo. In addition, the state of the other concentric bands, as the echo range reflects the existence of other molecular structures in the target space field of view at the host sensor junction that are uniquely signified by the probe energy type associated with the assigned color in the time frame of the current probe interval, will simultaneously appear on the type of biological radar display monitor shown in FIG. 12. This target-cell vector pointer 9 informs the user of a specific detail of metabolic activity in the field-of-view.

Furthermore, there are some known properties of the optical spectrum, band 4 represented by the color blue, that distinguish light phenomena from the other partitions in several ways. First light possesses a minimum of nine levels of discrimination, one for each color, which allows the implementation of 41 in a probe interval without the other bands. For example 9A being the states of band 4 at the instant of appearance of 9 in the ultraviolet band 3, can be shown in association with all the other colors of band 4 (sub channels) and still be shown in the ultraviolet spectrum. Knowledge of the results of probing in the optical band is not dependent on knowledge of the associated results of concurrent probing in the other bands but is directly known, whereas for the other bands the optical band is used to indicate the results of non band 4 probing. Band 3, 136 and Band 5, 134 are at the fringes of band 4 may be expected to evince a share of this property. With respect to the other bands 130, 131, 132, 133, 137 and 139 an analogical annunciator format may be used comprised of a spectrum of transducer types which are characteristic of these bands, similar to the optical spectrum display described in 41, with methodical sequences of touch, sound, beyond sound pulse, heat gradients, radio detectable emissions, and sequences of memory associative images and odors may be used similarly to annunciate the events that take place at the host sensor junction 127. Also light travels at speeds near or at the operating speed of state of the art computers making it a highly efficient data acquisition means using fiber optic transmission systems. Also there exist highly sensitive means for manipulating sensor bearing catheters at the levels of physical discriminating required to scan interior segments of cells. Incorporate by reference to such existing means in the following inventions:

1. U.S. Pat. No. 4,084,209
2. U.S. Pat. No. 3,926,040
3. U.S. Pat. No. 4,172,630
4. U.S. Pat. No. 4,112,291

Also light performs in accordance with the laws of classical electromagnetic fields, pronounced in Maxwells Equations of Electromagnetic Fields in the sense of the macroscopic field domain, and simultaneously obeys the modern statistical laws of quantum mechanics embraced in the wave equation known as Schroedilgers equation in modern particle physics so that light is the preferred domain of the physical spectrum in the preferred embodiment of this invention while it is however by no means unique, with respect to the means revealed in this disclosure.

Referring now to FIG. 10, biological radar 41 is shown to be comprised of experiment-machine jogging algorithm 163A which jogs the scan of the host sensor junction 127 with scanning patterns of originating probe energy originating from 166 and experiment-machine jogging algorithm 163B which jogs the scan of the resultant echo of 166 from host sensor junction as such echo is detected from probe energy detector 167. In correspondence with the operation of the probe energy channel selector 22, the energy signal in a probe interval may be a combination of k out of 10 signal types where $1 \leq k \leq 10$, and 10 is the number of domains in the partitioning of the physical spectrum. The probe interrupt selector channel 23, not shown in this drawing is a function of pics 22 modulation which uses the integration band (also called null) to associate a set of specific permuted operating sequences of a currently selected combination of signal types as being the characteristic information channel uniquely signifying the identity of the targeted cell with respect to molecular identification and physical context. The physical spectra existing in the probe interrupt selector channel in an incremental instant of the current probe interval is the real time molecular signature of the actual molecule being pointed at. Thus 164 shows the target range of 163A of the current probe interval while 165 shows the echo range of 163B. PICS, CICS and CID, when the cancer experiment is in flight, 22, 116, and 85 respectively synchronize and coordinate the operation of biological radar 41 as shown in detail in other figures and as described. Platform stabilizer facility 168 operates in synchronization with 166 and 167, which are directly controlled by PICS 22 since the feedback from 168 which indicates a shifting of a field-of-view requires adjustments of 166 and 167 to restore the selected target cell to its preshifted position in the field-of-view. This adjustment is made with respect to every band in the permuted sensor group combination active at the instant the shift is detected. Interdomain controller 169, a setp in flow chart of CICS, FIGS. 20, 21, 22, 23, and 24, 116 synchronizes the operation of 168 in parallel operation with 22, 166 and 167, this synchronization with respect to cell types 86, 87 and 88. When a stable state is achieved, there will be three selected target cells of the desired type in a selected field of view and an immunology experiment may be begun by the manipulation of carcinogenic induction driver, 85.

Figure 12:
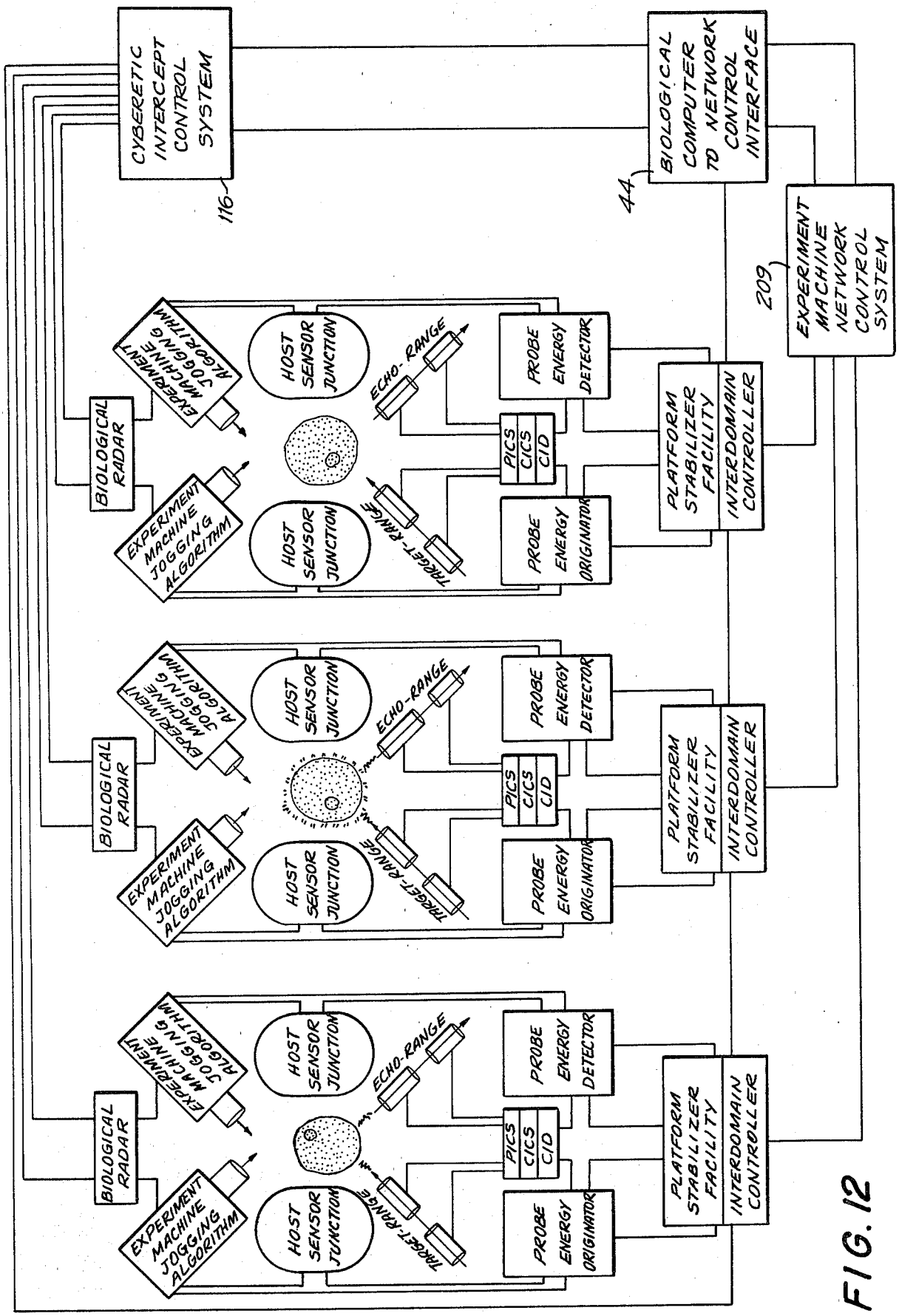
FIG. 12 is a function block diagram of a biological computer.

Referring now to FIGS. 10, 11, and 12, biological radar for calibration 41A, control 41B, and experiment 41C cells, correspondence with reference numerals on FIGS. 8 and 23 are 1 to 1 with the exception of reference numerals 172 through 201 inclusive. Reference numerals 172–176, 182–186, and 192–196 correspond to 164 on FIG. 10. Reference numerals 177–181, 187–191, and 197–201 correspond to 165 on FIG. 10. The definitions of these reference numerals correspond to the description of the PICS 22 as follows in FIGS. 8 and 9.

172, 182, 192: Probe energy entry window
173, 183, 193: First half interval flight of probe energy
174, 184, 194: Half interval probe energy window
175, 185, 195: Second half interval probe energy flight
176, 186, 196: Host sensor junction probe energy window
177, 187, 197: Host sensor junction detector energy window
178, 188, 198: First half interval flight of echo spectra
179, 189, 199: Half interval echo spectra window
180, 190, 200: Second half interval echo spectra
181, 191, 201: Detector energy exit spectra window Reference numeral 202 in FIG. 11 biological computer, corresponds to CICS 116, biological computer to network control interface 44 and experiment machine network control system 209, all taken collectively which comprises the disclosure of the biological computer 202 including the in vivo real time dynamic scanning of target cells 86, 87 and 88.

Referring now to FIG. 13, 86, 87 and 88 are three targeted cells at the host sensor junction 127 field-of-view of the current probe interval. The pics 22 is set up for the currently selected group of scan bands corresponding to the associated sensor arrays of the current target selection choosing one or more from 130 through 139 in a permuted sequence consistent with the molecular structure previously observed in prior probe-intervals. Biological radar 129 is set up to receive the corresponding echo-spectra of the associated detector arrays for the permuted sensor group of the current probe interval. In a direct information exchange with kinetic sensor controller 2, and likewise by indirectly with kinetic sensor positioning facility 1, and experiment platform positioning facility 125, biological radar 129 generates compensation signals and validation signals for communication to pics 22 through reference band 139, and null band 138 called elsewhere the integration band, and with commands it originates and transmits to controller 2, cybernetic intercept control system 116 is so informed with all of the information it requires to coordinate platform positioning, sensor manipulation, molecular tracking, target cell scanning, resolving of relative motion, distribution of information to the network workstation and collection of feedback from the clusters of network workstations. For the current probe interval, 116 does an information exchange with sensor group topology data base 70 for real time parameters of the currently operating transducer arrays and with code mode leveler driver module 140 to correctly format the acquired data for the user defined network distribution protocol. The real-time echo burst data is thus structured into reality 89, algorithm 99 and calibration 91 spectrums according to the results of the current probe interval scan of 86, 87 and 88. The orderly management of these three spectrums 89, 90 and 92 is maintained in a common format called levelled sensor group signal burst 142, known in the art as signal averaging, and multiplexed in a group matrix format descriptive of the permuted combination of sensors active in the current probe interval by signal-group burst-detector 145, and leveled sensor-group signal-burst digitizer 146, and then digitally filtered into digitized signal group staging buffer 144, for continuance of down stream processing in the direction of the network workstation nodes. The communication scheduler 147, and communication handler 151 of (44) facilitate the handling of data through the information paths that are down stream from the real-time metabolic process that originated the data being handled. The respective signal group monitors 148, 149 and 150 of experiment, calibration, and control models dispatch an image of the data they monitor to subsidiary clocking facilities 152, 153 and 154 for time-stamping and real time incorporation into biological computer historian 155 which must be a real time large data base computer, dedicated to the overseeing of these down stream network observation processes. Through access to 155, experiment machine interface controller 47, and biological computers of experiment machine coupling matrix 156 operate in concert to send images of current probe interval informational activities to information network distribution facilities calibration 157, control 158, and experiment 159 and to the real time data bases 160, 161 and 162. It is possible for the user to switch the roles of the calibration, control and experiment cells in-flight as long as a record of this type of event is coordinated by biological computer historian 155, and that real time updates to data bases 160, 161 and 162 are consistent with these switching type events. It is of the utmost importance for the users of this invention to remember that the originating metabolic process which is the target process of the experiment machine network system does not abate to accommodate the information processing needs of down stream processing; all events described take place within the time constraints of the currently active probe interval, images of probe intervals are available from historian 155 upon demand from console 42 and to segments of information distribution network workstations when specified by user defined network interface protocol.

Referring now to FIG. 14 multimode-selectable sensor-driven message-multiplexed modulation/detection-focused signal-selected spectra-widebanding-facility 108 shows generic positional relationships of components of the network system without characterizing the details of sensor operation with a carcinogenic experiment. Target cell selection processor 101 receives from jogger 93 information concerning mode of signal propagation, operating sensor-group, signal attributes, focusing parameters, selection parameters, signal flight direction, channel identification, time-spectrum of the probe interval, and status of molecular radar control system 115. Target cell algorithms 102 and 103 operate under the control of 101. Carcinogenic induction driver 85 continuous algorithm spectrum 109, statistical algorithm spectrum 111, quantum algorithm spectrum 112, and relativity algorithm spectrum 110, receive information from 93, perform their function in the experiment and in real time report the consequences of their operation to molecular conversion map 113. The process clock 28 receives a report of the active molecules being aimed at in the current probe interval and formats a time spectra record of this information along with spectra parameter translation 124 and channel function distribution information 114 and dispatches this information to the pics 22 in a format 22 expects. Control system 115 sends the stabilization parameters of the record it receives to platform stabilizer coupler 125 and sensor aiming parameters to sensor-to-host coupling matrices 126. The operation of 115, 125 and 126 in the current probe interval results in three information inputs into 23 probe interrupt selector channel. The cybernetic interrupt control system 116 decodes the information received from 23 and combined with information exchanges that are made between detection system 117 and raw data comparator logic 118 exchanges information about the current probe interval activity with data base intercept facility 119, interactive command interaction decoder 120, metabolic process command facility 122, interactive command interception facility 121, and thematic graphics display facility 40, 41, 48, 49 and 68. Network workstations input/output nodes 123 are a network of observation stations where representations of the activities of the current probe interval are annunciated and indications of observations made at these stations are entered into the system so as to be fed-back and considered in the next probe interval. Thus FIG. 14 can be read from the bottom starting with 123 going upwards with the same significance as starting at the top 108, and reading downwards. The return path from 123 is ultimately back to cybernetic jogging model 93.

TRACING THE CARCINOGENIC DEVELOPMENT AND EXPLORING THE INTERIOR OF A CELL

Tissue Space

The target of a probe is a cell-type space. Thus, the constitution of the subject tissue space is of cardinal importance.

The virgin characteristics of a targeted cell space data-base derive solely from the cell-differentiation sequences preceeding. Additional attributes are derived by originated intrusions by foreign substances or externally applied force. In any case, the cell kinetic differentiation sequences in a time interval form the cell clusters which comprise the constitution of the targeted field-of-view.

Thus, there are cells in different stages of physical and chemical development, as well as of different generic types that form the tissue, muscle, blood, marrow, skin, hormone, and other required structures to compose the organs which lend the host its physical and chemical nature.

A means this invention provides is the ability to dynamically select a physical domain and scale that is appropriate to the cells that present themselves in the tissue-space that is the target of an experiment-machine probe: this is inclusive of automated methods of cell classification. The following diagrams illustrate the means. FIG. 8 shows a cell type subjected to a multidomain scan, as do FIGS. 13 and 3. It can be seen that, depending on the size of the cell relative to the size of the scale, a different result will be observed. Only one can be correct, and that one posesses the range and characteristics that yield the reality of the cellular metabolism comprising the tissue space being probed. Clearly, the characterizing theme of a probed target space is that it is microscopic in the metabolic domain. Thusly, experiment-machine sensors have components that can resolve required parameters at both micro and macro levels.

Figure 19:
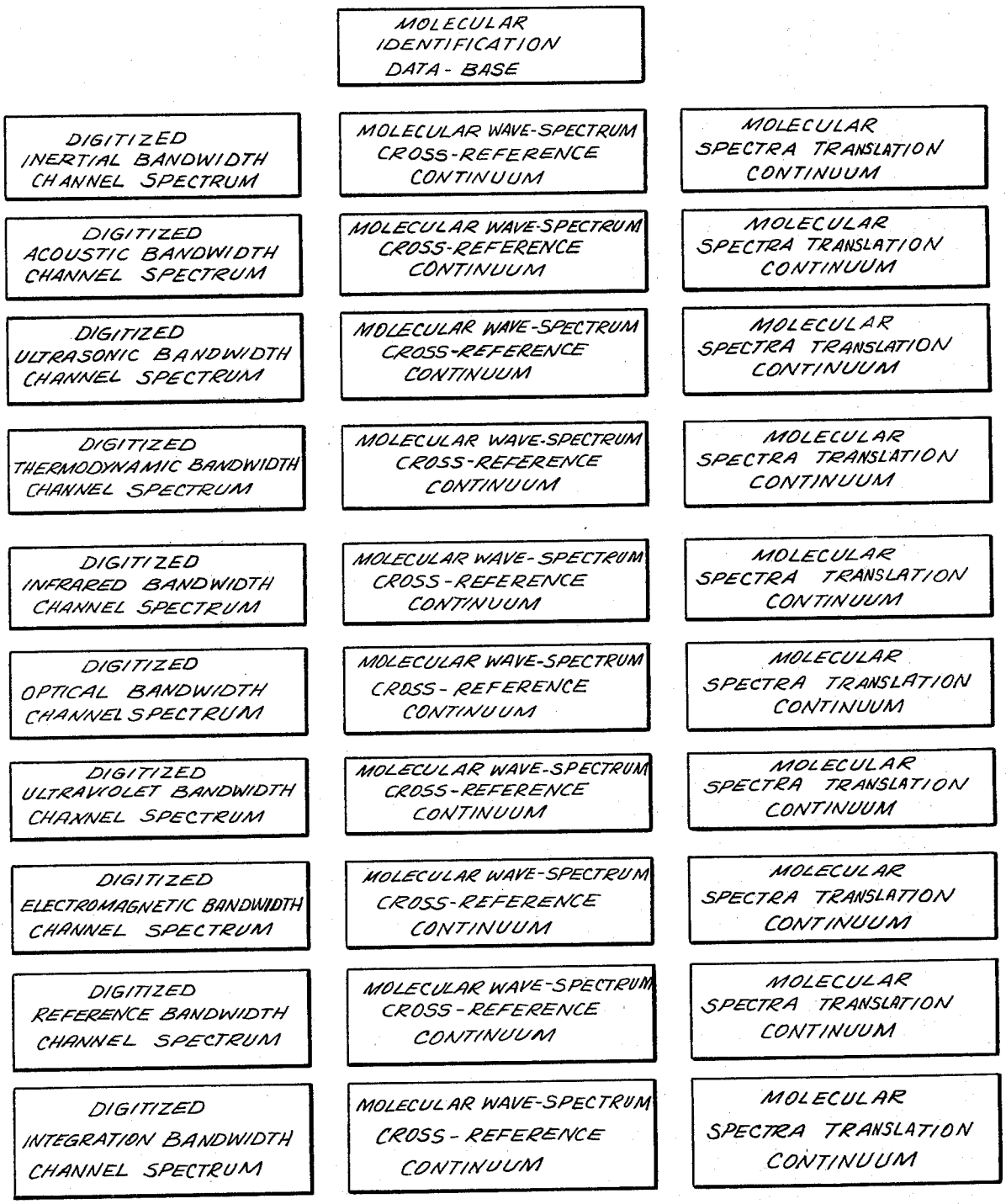
FIG. 19 is a flow chart of molecular identification data base used by radar control system.
Figure 20:
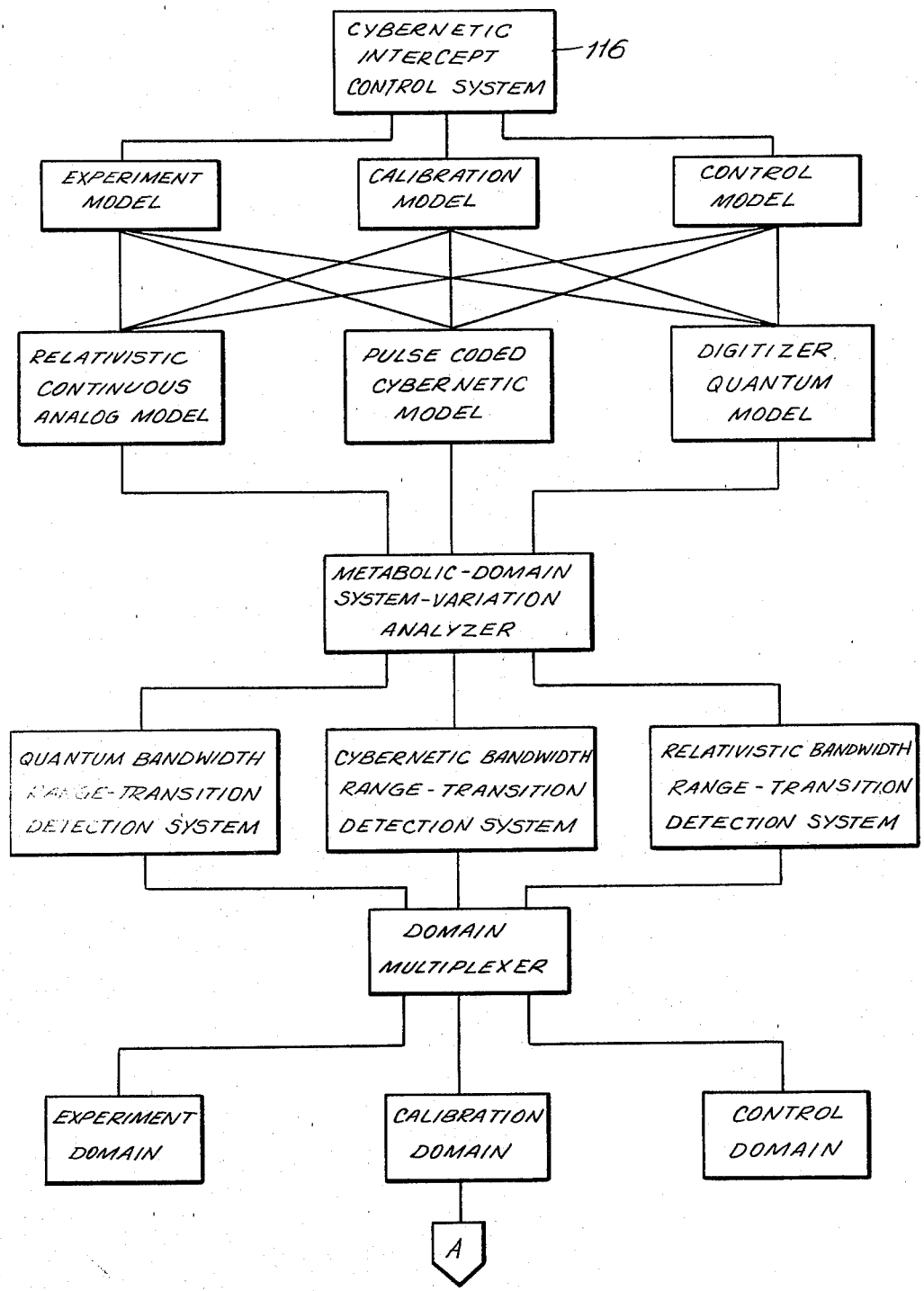
FIG. 20 is a flow chart of the cybernetic intercept control system.
Figure 21:
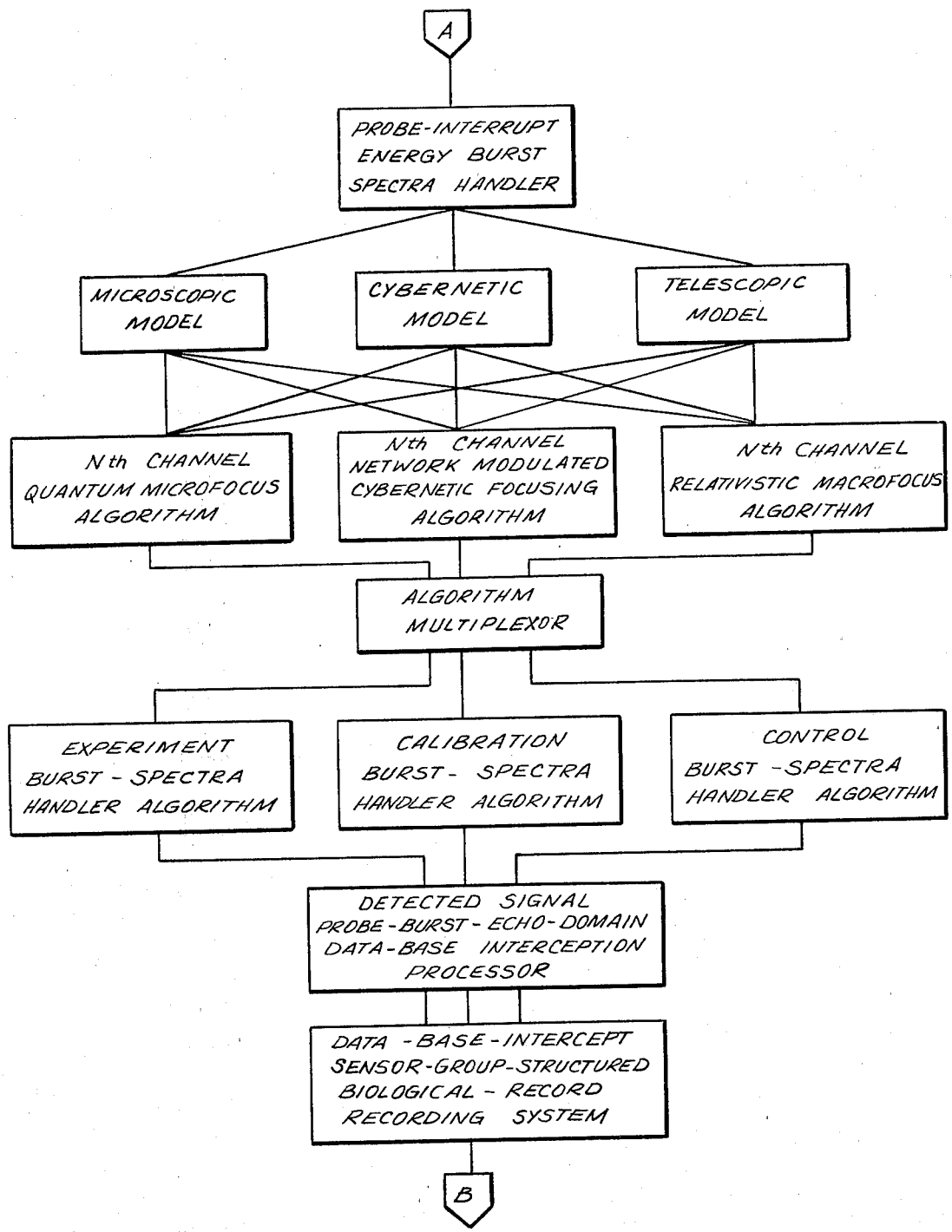
FIG. 21 is a flow chart which is a continuation of FIG. 20.

FIGS. 8 and 19 show the division of sensor types by their generic classification corresponding to partitioning of the physical spectrum. Each generic class is referred to as a sensor group. Each group is further subdivided into channels within the sensor group to provide a gradient of resolving-powers in that sensor group so as to be able to automatically select, upon command, the most appropriate (i.e. reality resolving) sensor channel for the current position in the subject target space. This means of stratified classification in each of the ten sensor groups, reflects the proliferated structural classification that drives the Probe-Interrupt-Channel Selector effectively. This means provides the enriched proliferation of the numerous variety of machine-states that is necessary to track the processes of cell kinetics.

PROBE INTERRUPT CHANNEL SELECTOR (PICS)

This component of a Biological Computer is embodied in firmware coupled to the computer sensor-coupling matrix that is an adjunct to the CPU of a biological-computer. Its function corresponds and is somewhat analogous to, the I/O controllers known to those versed-in-the-art of general purpose digital computers. A VLSI may have the fearture built in as it is fabricated.

In general purpose digital computers, the I/O controllers function to manage the peripheral facilities used in support of communication of information between the CPU, and the hi-speed and main memory and auxilliary storage facilities, and human interfacing terminals such as teletypes, video terminals, radar-set sweep-pattern display terminals with data-entry capability supporting two-way communication, and a plurality of data input and recognition annunciator stations.

In a Biological Computer, it is the primary responsibility of the PICS and CPU to converse with the states of the ten sensor-groups in such a way so as to be able to read the state of any permutation and combination of sensor group sub-channel or sub-channels. In addition, to be able to, on demand, place command signals at the beginning of the channel on a path that terminates at the outer boundary of the specific sensor that is attached to that command sub-channel. In addition, each sub-channel supports both analog (i.e. continuous signal) or a digital (i.e. pulse coded) signal transmission. At any given instant, any permuted combination of digital (PCM) or analog (continuous) signal transmission and associated processing that occur in each of the ten sensor groups, and within each group, forms an acquired data segment.

Figure 16:
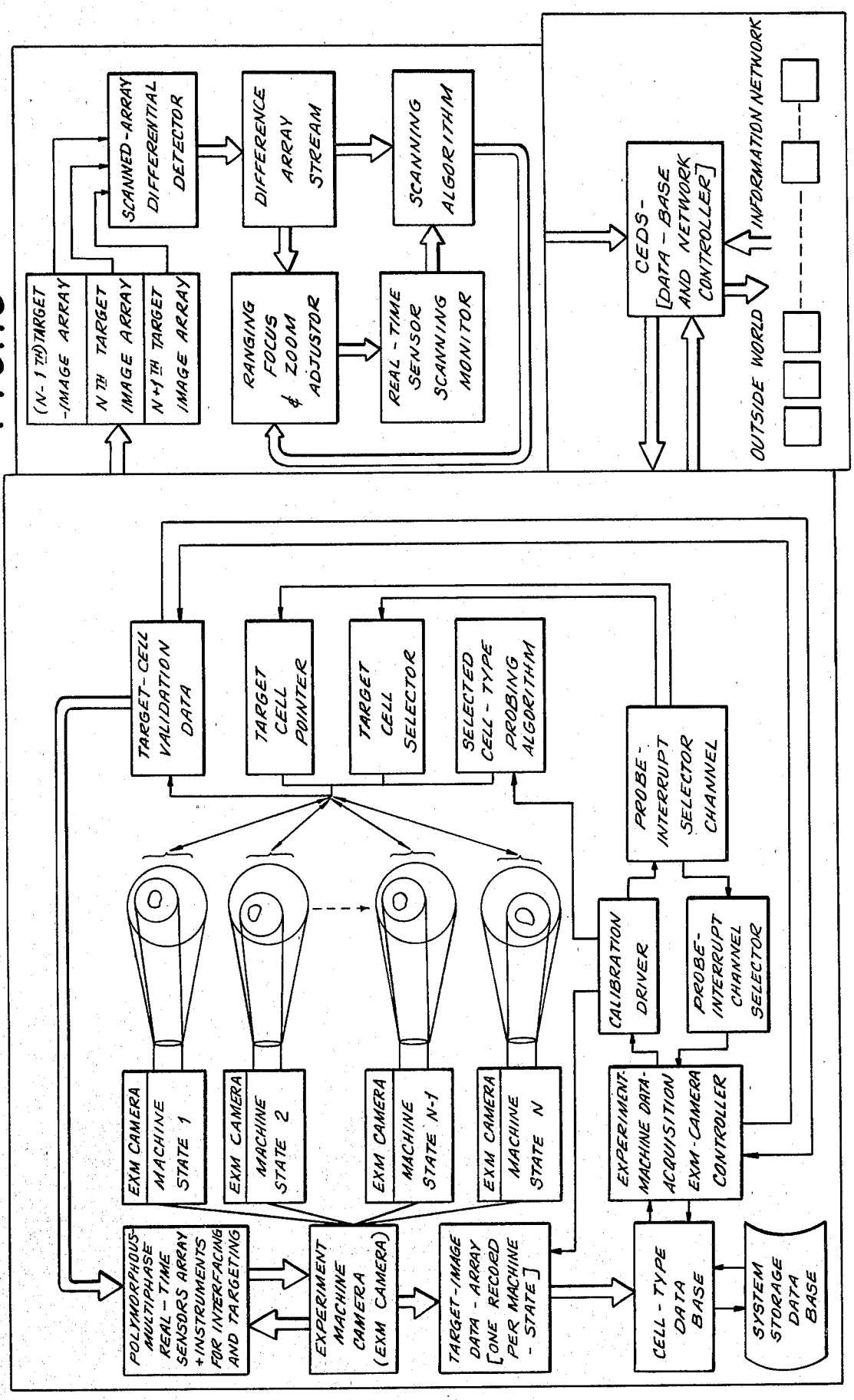
FIG. 16 is a flow chart of the journey of acquired data between targeted cells and a user network.

The specific details of these possible combinations is a function of the physical nature of the sensor, the set of algorithms selected to control these sensors, see FIG. 4, the chemical condition of the subjected target-space being probed, and the accuracy and precision chosen for the current data, and the contents of the data-base shown in FIG. 16.

THE PRIMARY ANALOG-EMBODYING THE VITAL ANALOG

The optical band visibility is the cardinal reference perspective on which objective information rests. However, the other nine partition sub-bands of the physical spectrum own a measure of cardinality. Mechanical-models, multidomain analogs, (i.e. electro-acoustic, see U.S. Pat. Nos. 4,172,386, 4,096,756, and 4,111,050) and extended mapping technologies derive from the human ability to interact with mapped symbolic representations of a perceived reality. It is because we can see, feel, and hear, that this is evident. The substantive nature of light media, as has been shown to be of dual character, (processing both particulate and continuous wave form attributes) is the base-line contextual background and foreground that surrounds inventions which demonstrate the postulate of visual-reference. The fact that there are multivariate pluralities of these analogies demonstrates this position. The fact that we can construct mathematical (symbolic) models to negotiate the human interface to control and manipulate the subsequently resulting pluralities of machines, is perhaps the strongest evidence that the apparent visible reference is the primary source of knowledge. In examining this proposition, we find that the mind or brain that is behind the eyes that are prerequisite to vision, shape the reality that is reported in the field of visible reference. Through as an entity is an attendant factor that cannot be overlooked in an invention of this type. The apparent dual nature of light must be examined in this context of the visual analog to metabolic communication to determine, if the apparent duality nature of light is a result of the prior biological dual-nature of human-mind, or if the opposite is true; or if in fact both cases are simultaneously true. The experiment-machine is a means to algorithmically execute in its memory, the substance of the preceding propositions to extract the hypothesis of measure and validation that best fits the current process environment. Visibility is not the only criteria, since the interaction of a visible-reference with now visible facts raises issues that cannot be within the visible-spectrum alone, such as energy transfer, surface tension and density.

In the case of a single host-resident living cell, it is not realistic since any cell is co-resident in a host with all the other cells. When healthy, each functions in concert with all the others. In the course of time, metabolism, mitosis, waste disposal and replication are among the cell kinetic micro-vehicles of the developmental organic macro-process; the organic macro-process, in turn, when healthy creates and sustains these continued micro-processes attendant with corresponding micro-vehicles.

The male-female nature of existence, and the right and left molecular polarity of Louis Pasteur, appear to be evidence of the dual nature of light. When investigating the cell-interior nuclear composition of chromatin, we find a double helical architecture, i.e. (another duality) dominating all aspects of cellular existence. Then the following means must be described. My invention describes these and other attributes by algorithmically testing the consequences of its probes, providing a means to answer the following questions:

1. How do cells keep time or know when to divide?
2. What are the laws or principles of symbiotic contention that ultimately arbitrate which cells die, and which should continue uninterrupted and which mutate all other issues of metabolic importance?
3. What are the recognition mechanisms used by a cell to arbitrate the identification needs of metabolic processes?
4. Which cells are slaves and which are masters? What cell types, in what combination and in what temporal order are required to act in concert?
5. What are the recognition mechanisms that detect anamolies in required cell annunciation protocol? How can we format the sequences of these recognition mechanism into an interface protocol?
6. How can we simulate the attendant biological communication network, so as to be in a virtually conversational mode with a specific host's metabolic communication network?

The means to these and to a plurality of correlated means are controlled by the apparatus chosen by using a plurality of clusters of biological-computers which control clusters of pluralities of sensor-groups to interact with a host to produce pluralities of pulsed and continuous echo signals which are intercepted by detection monitors that format these pluralities of echo signals into biological records so that they may become records or segments on data-base and transmitted throughout a human intervening communication network. An event in the host becomes known by the appearance of the associated biological-record some place in the network of bioradar observation workstations.

The commandering of the data-communication network and the contents of the data-base becomes an image of the host's biological-communication network in the real-time domain, and the human intervening network becomes a probe of the host's biological communication network. Clearly, the state-of-the-art of the sensors used will determine the effectiveness of the future embodiments of the experiment-machine's Real-Time Biological Message Interception Information Retrieval Network. FIGS. 2, 4, 5, 6, 7 and 21–24 show the means of this network.

What I claim exclusive property privilege for is:

1. A biological diagnostic and testing system comprising:
    probe means for examining intra-cellular activity within an individual cell in animal tissue in vivo and selectively providing a physical indication signal representing that activity;
    control means for selectively actuating said probe means to provide said physical indication signal; and
    display means for providing a visual display in real time of the intra-cellular activity represented by said physical indication signal.

2. The system according to claim 1:
    wherein said control means includes means for selectively delivering an interrogation signal, in the form of an energy burst, to said probe means; and
    wherein said probe means comprises transmit means for directing interrogation signal energy bursts delivered thereto toward a target area within said individual cell and receiver means for receiving, as said physical indication signal, a reflection of said energy burst from said target area.

3. The system according to claim 2 wherein said control means further comprises:
manipulator means for automatically maintaining said probe means directed toward said target area in spite of movement of said animal tissue.

4. The system according to claim 2 wherein said control means further comprises:
means for detecting changes in successive physical indication signals;
means for determining if the detected changes are the result of relative movement between said probe means and said animal tissue; and
manipulator means for re-positioning said probe means, in response to a determination of relative movement between said probe means and animal tissue, to maintain said probe means directed toward said target area.

5. The system according to claims 2 or 4:
wherein said probe means comprises at least first and second separate probe elements, each directed to target areas within respective individual cells in said animal tissue, each including transmit means responsive to energy bursts delivered thereto for directing such bursts toward the target areas of that probe element, and each including receiver means for receiving reflections of said energy bursts; and
wherein said control means includes multiplexer means for delivering energy bursts to said first probe element which differ in a physical parameter from energy bursts delivered to said second probe element.

6. The system according to claim 5 wherein said energy bursts are light bursts and wherein said probe elements are fiber optic probes.

7. The system according to claim 6 wherein said physical parameter which differentiates energy bursts delivered to said first and second probe elements is time.

8. The system according to claims 2 or 4 wherein said probe means comprises at least first and second separate probe elements of different types, each probe element being directed to a respective target area within different individual cells in said animal tissue, each probe element including transmit means responsive to energy bursts delivered thereto for directing the delivered bursts toward the target area if that probe element, and each probe element includes receiver means for receiving reflections of said energy bursts, and wherein said energy burst delivered to said first probe element is a different energy form than the energy burst delivered to said second probe element.

9. The system according to claim 8 wherein said first probe element is a fiber optic probe and the energy burst delivered thereto is light energy.

10. The system according to claim 4 wherein said control means further comprises means for selectively expanding and decreasing the field of view of said target area.

11. A method of biological diagnosis and testing comprising the steps of:
examining intra-cellular activity within an individual cell in animal tissue in vivo with a probe and selectively providing a physical indication signal representing that activity;
selectively actuating said probe to provide said physical indication signal; and
providing a visual display in real time of the intracellular activity represented by said physical indication signal.

12. The method according to claim 11:
wherein said step of actuating includes selectively delivering an interrogation signal, in the form of an energy burst, to said probe; and
wherein said step of examining comprises transmitting interrogation signal energy bursts, delivered to said probe, toward a target area within said individual cell, and receiving, as said physical indication signal, a reflection of said energy burst from said target area.

13. The method according to claim 12 further comprising the step of:
automatically maintaining said probe directed toward said target area in spite of movement of said animal tissue.

14. The method according to claim 12 further comprising the steps of:
detecting changes in successive physical indication signals;
determining if the detected changes are the result of relative movement between said probe and said animal tissue; and
re-positioning said probe, in response to a determination of relative movement between said probe means and animal tissue, to maintain said probe directed toward said target area.

15. The method according to claims 12 or 14 wherein said probe comprises at least first and second separate probe elements, and further comprising the step of:
delivering energy bursts to said first probe element which differ in a physical parameter from energy bursts delivered to said second probe element.

16. The method according to claim 15 wherein said energy bursts are light bursts.

17. The method according to claim 16 wherein said physical parameter which differentiates energy bursts delivered to said first and second probe elements is time.

18. The method according to claims 12 or 14 wherein said probe means comprises at least first and second separate probe elements of different types, and wherein said energy burst delivered to said first probe element is a different energy form than the energy burst delivered to said second probe element.

19. The method according to claim 18 wherein the energy burst delivered thereto is light energy.

20. The method according to to claim 14 further comprising the step of selectively expanding and decreasing the field of view of said target areas.

21. A biological diagnostic and testing system for monitoring intra-cellular activity within a common host, said system comprising:
a plurality of individually actuable probe elements for examining intra-cellular activity within respective individual cells in said host, each probe element being responsive to reception of an interrogation signal for sensing a physical parameter within a localized area in its respective cell and providing a measurement signal representative of the state of that parameter;
control means for selectively actuating each of said probe elements with respective interrogation signals; and
processor means for receiving and individually monitoring the measurement signals provided by said probe elements.

22. The system according to claim 21 wherein said control means comprises multiplexer means for applying interrogation signals to said probe elements in a prescribed time sequence.

23. A method of biological diagnosis comprising the steps of:
   (a) selectively examining intra-cellular activity within an individual cell in animal tissue in vivo and providing an indication signal representing that activity;
   (b) comparing the provided indication signal with stored medical history data; and
   (c) determining, from the comparison in step (b) whether or not a predetermined disease condition is indicated by the examined intra-cellular activity.

24. The method according to claim 23 wherein step (a) includes:
   sequentially examining different areas within a cell and providing respective indication signal corresponding to the intra-cellular activity in each area.

25. The method according to claims 23 or 24 wherein step (a) includes:
   examining intra-cellular activity within plural individual cells of said host with respective individual probe members and providing respective indication signals from each probe member.

26. The method according to claim 25 wherein said predetermined disease condition is a carcinogenic condition.

27. The method according to claims 23 or 24 wherein said predetermined disease condition is a carcinogenic condition.

28. The method according to claims 23 or 24 wherein step (a) includes:
   selectively actuating a probe to provide said physical indication signal.

29. The method according to claim 28 wherein said step of actuating includes selectively delivering an interrogation signal, in the form of an energy burst, to said probe; and
   wherein said step of examining comprises transmitting interrogation signal energy bursts, delivered to said probe, toward a target area within said individual cell, and receiving, as said physical indication signal, a reflection of said energy burst from said target area.

30. The method according to claim 29 further comprising the step of:
   automatically maintaining said probe directed toward said target area in spite of movement of said animal tissue.

31. The method according to claim 29 further comprising the steps of:
   detecting changes in successive physical indication signals;
   determining if the detected changes are the result of relative movement between said probe and said animal tissue; and
   re-positioning said probe, in response to a determination of relative movement between said probe means and animal tissue, to maintain said probe directed toward said target area.

32. The method according to claim 31 wherein said probe comprises at least first and second separate probe elements, and further comprising the step of:
   delivering energy bursts to said first probe element which differ in a physical parameter from energy bursts delivered to said second probe element.

33. The method according to claim 29 wherein said probe comprises at least first and second separate probe elements, and further comprising the step of:
   delivering energy bursts to said first probe element which differ in a physical parameter from energy bursts delivered to said second probe element.

34. The method according to claim 33 wherein said energy bursts are light bursts.

35. The method according to claim 34 wherein said physical parameter which differentiates energy bursts delivered to said first and second probe elements is time.

36. The method according to claim 31 wherein said probe means comprises at least first and second separate probe elements of different types, and wherein said energy burst delivered to said first probe element is a different energy form than the energy burst delivered to said second probe element.

37. The method according to claim 29 wherein said probe means comprises at least first and second separate probe elements of different types, and wherein said energy burst delivered to said first probe element is a different energy form than the energy burst delivered to said second probe element.

38. The method according to claim 29 further comprising the step of selectively expanding and decreasing the field of view of said target areas.

* * * * *